US010702231B2

(12) United States Patent
Ohishi

(10) Patent No.: US 10,702,231 B2
(45) Date of Patent: Jul. 7, 2020

(54) MEDICAL IMAGE PROCESSING APPARATUS, X-RAY DIAGNOSTIC APPARATUS, MEDICAL IMAGE PROCESSING METHOD AND X-RAY DIAGNOSTIC METHOD

(71) Applicant: TOSHIBA MEDICAL SYSTEMS CORPORATION, Otawara-shi (JP)

(72) Inventor: Satoru Ohishi, Otawara (JP)

(73) Assignee: Canon Medical Systems Corporation, Otawara-shi (CN)

(*) Notice: Subject to any disclaimer, the term of this patent is extended or adjusted under 35 U.S.C. 154(b) by 780 days.

(21) Appl. No.: 14/878,662

(22) Filed: Oct. 8, 2015

(65) Prior Publication Data
US 2016/0022236 A1 Jan. 28, 2016

Related U.S. Application Data

(63) Continuation of application No. PCT/JP2014/060203, filed on Apr. 8, 2014.

(30) Foreign Application Priority Data

Apr. 9, 2013 (JP) ................................. 2013-081571

(51) Int. Cl.
A61B 6/00 (2006.01)
G06T 7/00 (2017.01)

(52) U.S. Cl.
CPC .............. *A61B 6/486* (2013.01); *A61B 6/481* (2013.01); *A61B 6/504* (2013.01); *A61B 6/5205* (2013.01);
(Continued)

(58) Field of Classification Search
CPC ......... A61B 6/481; A61B 6/484; A61B 6/486; A61B 6/504
See application file for complete search history.

(56) References Cited

U.S. PATENT DOCUMENTS 8,050,474 B2    11/2011  Baumgart
8,488,853 B2 *   7/2013  Sato ..................... A61B 6/5264
                                                128/922
(Continued)

OTHER PUBLICATIONS

Office Action issued Oct. 4, 2016 in Japanese Patent Application No. 2013-081571.
(Continued)

Primary Examiner — Eric D. Bertram
(74) Attorney, Agent, or Firm — Oblon, McClelland, Maier & Neustadt, L.L.P.

(57) ABSTRACT

According to one embodiment, a medical image processing apparatus includes processing circuitry. The processing circuitry obtains first and second blood vessel image by image generation processing which obtains time phase changes in concentrations of a contrast agent based on X-ray contrast image and generates time phase image according to a gray or color scale. The time phase image has pixel values corresponding to time phases at which the concentrations of the contrast agent become a specific condition. The image generation processing is performed multiple times based on X-ray contrast images acquired at different times. Further, the processing circuitry determines or corrects pixel values or time phases of at least one of the first and second blood vessel image, to make a pixel value of a time phase of the first blood vessel image coincident with that of the second blood vessel image.

15 Claims, 12 Drawing Sheets

(52) U.S. Cl.
CPC .......... *A61B 6/5211* (2013.01); *A61B 6/5217* (2013.01); *G06T 7/0016* (2013.01); *G06T 2207/10116* (2013.01); *G06T 2207/30101* (2013.01)

(56) References Cited

U.S. PATENT DOCUMENTS

| | | | | |
|---|---|---|---|---|
| 9,433,392 | B2* | 9/2016 | Ohishi | A61B 6/463 |
| 2009/0074267 | A1* | 3/2009 | Pedrizzetti | A61B 5/055 |
| | | | | 382/128 |
| 2009/0110252 | A1* | 4/2009 | Baumgart | A61B 6/481 |
| | | | | 382/130 |
| 2009/0297004 | A1* | 12/2009 | Baumgart | A61B 6/463 |
| | | | | 382/130 |
| 2012/0257809 | A1* | 10/2012 | Miyamoto | G06T 5/009 |
| | | | | 382/132 |
| 2013/0046176 | A1* | 2/2013 | Mistretta | A61B 6/032 |
| | | | | 600/431 |

OTHER PUBLICATIONS

International Search Report issued Jun. 10, 2014 in PCT/JP2014/060203 filed Apr. 8, 2014, with English Translation.
Written Opinion issued Jun. 10, 2014 in PCT/JP2014/060203 filed Apr. 8, 2014.
International Preliminary Report of Patentability and Written Opinion issued Oct. 22, 2015 in PCT/JP2014/060203 (English translation only).
Combined Chinese Office Action and Search Report dated Sep. 19, 2017 in Chinese Patent Application No. 201480020352.1 (with English translation of Category of Cited Documents).

* cited by examiner

MEDICAL IMAGE PROCESSING APPARATUS, X-RAY DIAGNOSTIC APPARATUS, MEDICAL IMAGE PROCESSING METHOD AND X-RAY DIAGNOSTIC METHOD

CROSS REFERENCES TO RELATED APPLICATIONS

This is a continuation of Application PCT/JP2014/60203, filed on Apr. 8, 2014.

This application is based upon and claims the benefit of priority from Japanese Patent Application No. 2013-081571 filed on Apr. 9, 2013; the entire contents of which are incorporated herein by reference.

FIELD

Embodiments described herein relate generally to a medical image processing apparatus, an X-ray diagnostic apparatus, a medical image processing method and an X-ray diagnostic method.

BACKGROUND

DSA (Digital Subtraction Angiography) is known as one of imaging methods for blood vessels in an X-ray diagnostic apparatus. DSA is the technology to generate subtraction image data between frames of X-ray image data before and after injecting a contrast agent into an object, for diagnosis. That is, X-ray image data are acquired before injecting a contrast agent as a mask image data for generating subtraction image data. On the other hand, X-ray contrast image data is acquired by injecting the contrast agent. Then, DSA image data is generated for diagnosis by subtraction processing between the X-ray contrast image data and the mask image data.

Such DSA image data can be generated as image data in which unnecessary anatomies in observation of a blood vessel are removed. That is, diagnostic image data in which blood vessels enhanced by a contrast agent are depicted selectively can be obtained. Consequently, images useful for diagnosis of a blood vessel can be displayed.

PRIOR TECHNICAL LITERATURE

[Patent literature 1] U.S. Pat. No. 8,050,474 B2

An object of the present invention is to provide a medical image processing apparatus, an X-ray diagnostic apparatus, a medical image processing method and an X-ray diagnostic method which can effectively utilize respective X-ray images acquired by X-ray imaging performed repeatedly at different times, such as before and after treatment.

DETAILED DESCRIPTION

Figure 1:
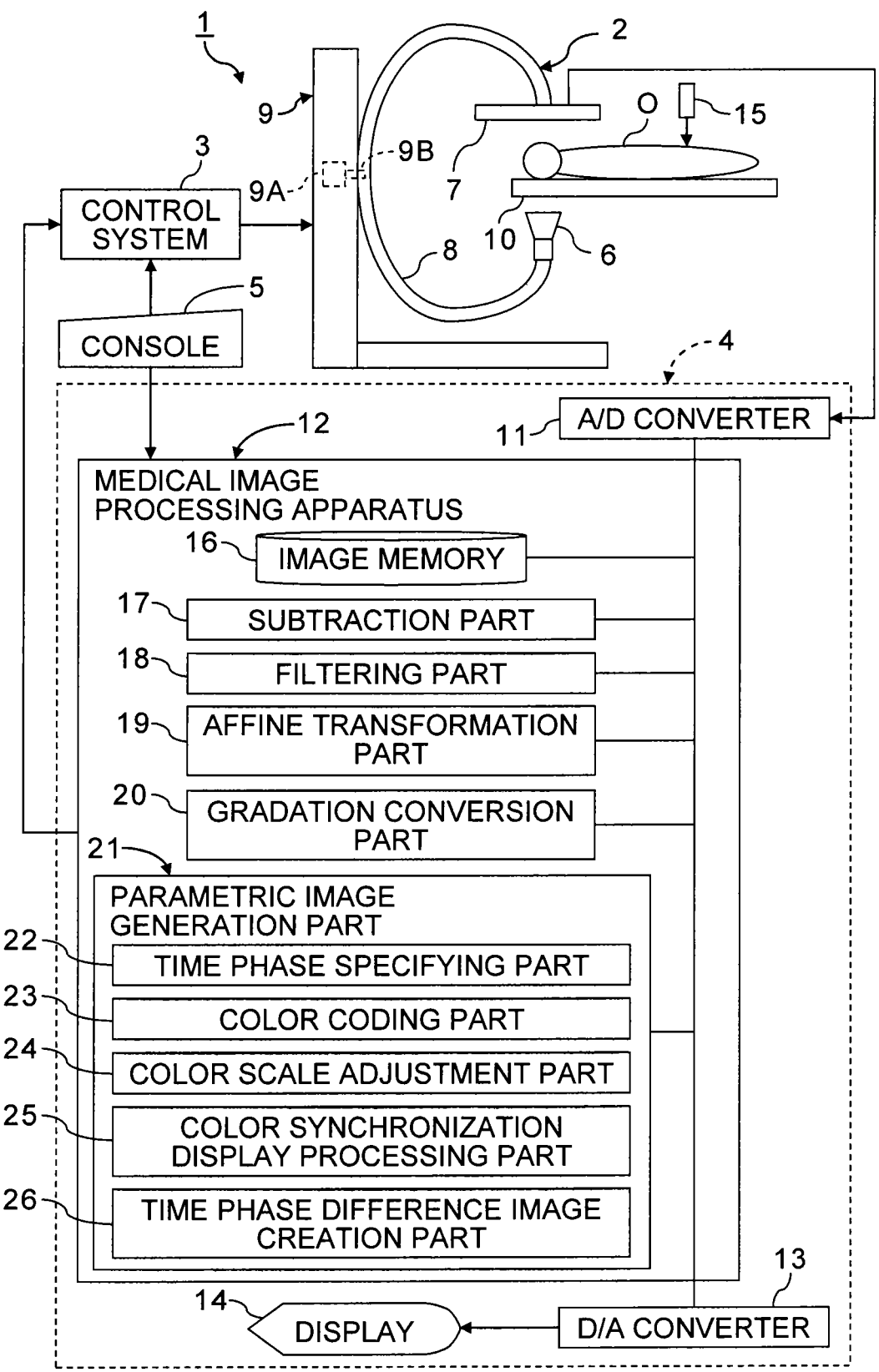
FIG. 1 is a configuration diagram of an X-ray diagnostic apparatus and a medical image processing apparatus according to an embodiment of the present invention.

In general, according to one embodiment, a medical image processing apparatus includes processing circuitry. The processing circuitry is configured to obtain first blood vessel image data and second blood vessel image data by image generation processing which obtains time phase changes in concentrations of a contrast agent based on at least X-ray contrast image data and generates time phase image data according to a gray scale or a color scale. The time phase image data have pixel values corresponding to time phases at which the concentrations of the contrast agent become a specific condition. The image generation processing is performed multiple times based on at least X-ray contrast image data sets acquired at different times. Further, the processing circuitry is configured to determine or correct pixel values or time phases of at least one of the first blood vessel image data and the second blood vessel image data, in order to make a pixel value of a time phase of the first blood vessel image data coincident with a pixel value of a corresponding time phase of the second blood vessel image data.

Further, according to one embodiment, a medical image processing apparatus includes processing circuitry. The processing circuitry is configured to obtain first blood vessel image data and second blood vessel image data by image generation processing which obtains time phase changes in concentrations of a contrast agent based on at least X-ray contrast image data and generates time phase image data according to a gray scale or a color scale. The time phase image data have pixel values corresponding to time phases at which the concentrations of the contrast agent become a specific condition. The image generation processing is performed multiple times based on at least X-ray contrast image data sets acquired at different times. Further, the processing circuitry is configured to generate subtraction image data having pixel values corresponding to differences in the time phases, at which the concentrations of the contrast agent become the specific condition, between the first blood vessel image data and the second blood vessel image data.

Further, according to one embodiment, an X-ray diagnostic apparatus includes an X-ray tube, an X-ray detector and processing circuitry. The X-ray tube and the X-ray detector acquires at least X-ray contrast image data from an object. The processing circuitry is configured to obtain first blood vessel image data and second blood vessel image data by image generation processing which obtains time phase changes in concentrations of a contrast agent based on the at least X-ray contrast image data and generates time phase image data according to a gray scale or a color scale. The time phase image data have pixel values corresponding to time phases at which the concentrations of the contrast agent become a specific condition. The image generation processing is performed multiple times based on at least X-ray contrast image data sets acquired at different times. Further, the processing circuitry is configured to determine or correct pixel values or time phases of at least one of the first blood vessel image data and the second blood vessel image data, in order to make a pixel value of a time phase of the first blood vessel image data coincident with a pixel value of a corresponding time phase of the second blood vessel image data.

Further, according to one embodiment, a medical image processing method includes: obtaining first blood vessel image data and second blood vessel image data by image generation processing which obtains time phase changes in concentrations of a contrast agent based on at least X-ray contrast image data and generates time phase image data according to a gray scale or a color scale; and determining or correcting pixel values or time phases of at least one of the first blood vessel image data and the second blood vessel image data, in order to make a pixel value of a time phase of the first blood vessel image data coincident with a pixel value of a corresponding time phase of the second blood vessel image data. The time phase image data have pixel values corresponding to time phases at which the concentrations of the contrast agent become a specific condition. The image generation processing is performed multiple times based on X-ray contrast image data sets acquired at different times.

Further, according to one embodiment, an X-ray diagnostic method includes acquiring at least X-ray contrast image data from an object; obtaining first blood vessel image data and second blood vessel image data by image generation processing which obtains time phase changes in concentrations of a contrast agent based on the at least X-ray contrast image data and generates time phase image data according to a gray scale or a color scale; and determining or correcting pixel values or time phases of at least one of the first blood vessel image data and the second blood vessel image data, in order to make a pixel value of a time phase of the first blood vessel image data coincident with a pixel value of a corresponding time phase of the second blood vessel image data. The time phase image data have pixel values corresponding to time phases at which the concentrations of the contrast agent become a specific condition. The image generation processing is performed multiple times based on at least X-ray contrast image data sets acquired at different times.

A medical image processing apparatus, an X-ray diagnostic apparatus, a medical image processing method and an X-ray diagnostic method according to embodiments of the present invention will be described with reference to the accompanying drawings.

FIG. 1 is a configuration diagram of an X-ray diagnostic apparatus and a medical image processing apparatus according to an embodiment of the present invention.

An X-ray diagnostic apparatus 1 includes an imaging system 2, a control system 3, a data processing system 4 and a console 5. The imaging system 2 has an X-ray tube 6, an X-ray detector 7, a C-shaped arm 8, a base 9 and a bed 10. In addition, the data processing system 4 has an A/D (analog to digital) converter 11, a medical image processing apparatus 12, a D/A (digital to analog) converter 13, and a display 14. Note that, the A/D converter 11 may be integrated with the X-ray detector 7.

The X-ray tube 6 and the X-ray detector 7 are settled at both ends of the C-shaped arm 8 so as to be mutually opposed at both sides of the interjacent bed 10. The C-shaped arm 8 is supported by the base 9. The base 9 has a motor 9A and a rotation mechanism 9B. The motor 9A and the rotation mechanism 9B drive so as to rotate the X-ray tube 6 and the X-ray detector 7 fast into a desired position together with the C-shaped arm 8 like a propeller.

As the X-ray detector 7, a FPD (flat panel detector) or I.I.-TV (image intensifier TV) can be used. Furthermore, the output side of the X-ray detector 7 is connected with the A/D converter 11 of the data processing system 4.

The control system 3 drives and controls the imaging system 2 by outputting control signals to the respective elements consisting of the imaging system 2. The control system 3 is connected with the console 5 as an input circuit. Therefore, instruction of imaging conditions and the like to the control system 3 can be input from the console 5.

Then, the imaging system 2 is configured to expose X-rays toward an object O set on the bed 10 at mutually different angles sequentially from the rotatable X-ray tube 6 under control by the control system 3. In addition, the imaging system 2 is configured to acquire X-rays transmitting the object O from the plural directions sequentially as X-ray projection data by the X-ray detector 7. The X-ray projection data acquired by the X-ray detector 7 are output to the A/D converter 11 as X-ray image data.

Furthermore, a contrast agent injector 15 is provided in the vicinity of the object O set on the bed 10 in order to inject a contrast agent into the object O. Thus, X-ray contrast imaging of an object O can be performed by injecting a contrast agent from the contrast agent injector 15 into the object O. The contrast agent injector 15 can be also controlled by the control system 3.

Next, configurations and functions of the medical image processing apparatus 12 will be described.

The input side of the medical image processing apparatus 12 is connected with the output side of the A/D converter 11. Meanwhile, the display 14 is connected to the output side of the medical image processing apparatus 12 through the D/A converter 13. Moreover, the medical image processing apparatus 12 is connected with the console 5. Then, direction information required for data processing can be input into the medical image processing apparatus 12 by operation of the console 5.

Note that, aside from the medical image processing apparatus 12 built in the X-ray diagnostic apparatus 1 as illustrated in FIG. 1, a similar medical image processing apparatus as an independent system may be connected with the X-ray diagnostic apparatus 1 through a network.

The medical image processing apparatus 12 includes an image memory 16, a subtraction part 17, a filtering part 18, an affine transformation part 19, a gradation conversion part 20, and a parametric image generation part 21. The parametric image generation part 21 has a time phase specifying part 22, a color coding part 23, a color scale adjustment part 24, a color synchronization display processing part 25, and a time phase difference image creation part 26.

The medical image processing apparatus 12 having such functions can be configured by a computer reading a medical image processing program. That is, processing circuitry may be used to configure the medical image processing apparatus 12.

The image memory 16 is a storage circuit for storing X-ray image data acquired by the imaging system 2. Therefore, when non-contrast X-ray imaging has been performed, non-contrast X-ray image data is stored in the image memory 16. Meanwhile, when X-ray imaging has been performed with injecting a contrast agent into an object O, X-ray contrast image data is stored in the image memory 16.

The subtraction part 17 has a function to generate time series DSA image data, depicting contrast-enhanced blood vessels, by subtraction processing between non-contrast X-ray image data read from the image memory 16 and time series X-ray contrast image data.

The filtering part 18 has a function to perform desired filter processing, such as a high-pass filtering, a low-pass filtering, or a smoothing filtering, of arbitrary data.

The affine transformation part 19 has a function to perform affine transformation processing, such as a scaling, a rotation movement, and a parallel translation, of X-ray image data, according to direction information input from the console 5.

The gradation conversion part 20 has a function to perform gradation conversion of X-ray image data by referring to an LUT (Look Up Table).

The parametric image generation part 21 has a function to acquire time changes in concentration of a contrast agent based on time series DSA image data or time series X-ray contrast image data and a function to generate parametric image data, having pixel values corresponding to times at which the concentrations of the contrast agent become a specific condition, as blood vessel image data. The parametric image data are time phase image data on which color pixel values depending on time phases have been assigned to time phases at respective pixel positions when concentrations of a contrast agent become a specific condition, such as the maximum values.

For that purpose, the time phase specifying part 22 has a function to specify time phases, at which concentrations of the contrast agent become a specific condition, based on profiles indicating time changes in the concentrations of the contrast agent. Moreover, the color coding part 23 has a function to assign colors corresponding to time phases specified by the time phase specifying part 22. The color scale adjustment part 24 has a function to determine a color scale used for color coding in the color coding part 23.

The specific condition for assigning colors can be determined, according to diagnostic purposes, to concentrations of a contrast agent corresponding to time points when the contrast agent has flowed in or arrived at a focused blood vessel, concentrations of a contrast agent corresponding to time points when the contrast agent has flowed out from a focused blood vessel contrarily, or the like. For example, a time defining the specific condition can be a time when a concentration of a contrast agent becomes the maximum value, a predetermined ratio of the maximum value, or a threshold value.

Figure 2:
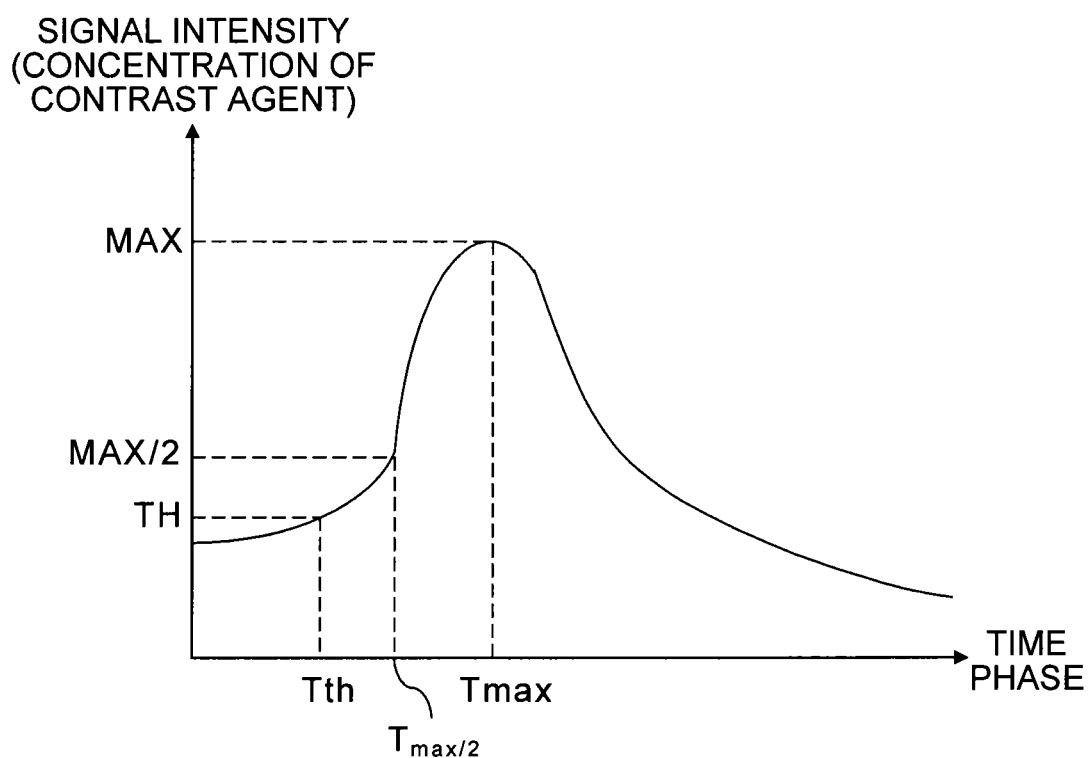
FIG. 2 shows a graph for explaining a method of identifying an inflow time or an arrival time of a contrast agent to a blood vessel based on a concentration profile of the contrast agent.

FIG. 2 shows a graph for explaining a method of identifying an inflow time or an arrival time of a contrast agent to a blood vessel based on a concentration profile of the contrast agent.

In FIG. 2, the horizontal axis shows the time phase direction while the vertical axis shows intensities of image signals, of DSA image data or contrast image data, representing concentrations of a contrast agent. As shown in FIG. 2, a profile in concentration change of the contrast agent can be obtained as a curve, showing signal intensities changing in time, by focusing a pixel corresponding to a blood vessel region of the time series DSA image data or contrast image data.

A typical concentration change profile becomes a curve of which the value increases gradually with the inflow of a contrast agent and decreases gradually with the outflow of the contrast agent. Therefore, when a threshold value TH for detecting a rising up of the curve is set for values of the concentration change profile, it becomes possible to identify a time phase at a start of contrast agent inflow into a focused blood vessel as a time phase Tth when the concentration of the contrast agent has reached the threshold value TH.

However, in a case that noises are large, the time phase at the start of a contrast agent inflow may be identified incorrectly. For this reason, a predetermined ratio within the range of 5% to 10% of the maximum value in a concentration profile of a contrast agent may be used for the threshold value so that influences of noises can be suppressed. Alternatively, a time phase Tmax at which a concentration of a contrast agent has reached the maximum value MAX or a time phase $T_{max/2}$ at which a concentration of a contrast agent has reached 50% of the maximum value MAX may be detected, from a concentration profile, as a time phase when the contrast agent has arrived at a blood vessel, as shown in FIG. 2. Hereinafter, an example case that an arrival time phase of a contrast agent is identified will be mainly described.

When the specification of a time phase, based on a concentration profile of a contrast agent, as shown in FIG. 2, is performed to each required pixel, and colors according to the specified time phases are assigned, parametric image data in which each blood vessel has been depicted in colors according to arrival times of the contrast agent or the like can be generated.

Note that, a time change in concentration of a contrast agent at each pixel representative of several pixels may be obtained by running average processing. That is, a matrix size of image data whose concentration changes of a contrast agent should be obtained can be minimized with smoothing processing. Moreover, concentration changes of a contrast agent may be obtained based on image data whose noises have been suppressed by low-pass filtering processing. These processing also can be said as running average processing and low-pass filtering processing of concentration profiles of a contrast agent in spatial directions.

The running average processing and the low-pass filtering processing can also be performed in not only spatial directions but also the time direction. In the case that the running average processing or the low-pass filtering processing is performed in the time direction, the processing is performed to concentration profiles of a contrast agent in the time direction.

Therefore, parametric image data can be generated based on time changes in concentration of a contrast agent after running average processing in at least one of the time direction and spatial directions. Moreover, parametric image data can be generated based on time changes in concentration of a contrast agent after low-pass filtering processing in at least one of the time direction and spatial directions. Thereby, smooth parametric image data from which the noises have been dramatically suppressed can be generated.

Moreover, parametric image data can also be generated based on time changes, in concentration of a contrast agent, each having a data interval shorter than a sampling interval of the concentrations of the contrast agent corresponding to an imaging interval of X-ray contrast image data. A time change, in a concentration of a contrast agent, which has a data interval shorter than a sampling interval of the concentration of the contrast agent, can be obtained by arbitrary processing, such as interpolation processing, curve fitting processing using a specific function, or gravity center calculation processing. Thereby, it becomes possible to identify an arrival time of a contrast agent or the like at each pixel with a higher precision. In particular, it is more effective in a case that at least one of running average processing and low-pass filtering processing is performed.

Figure 3:
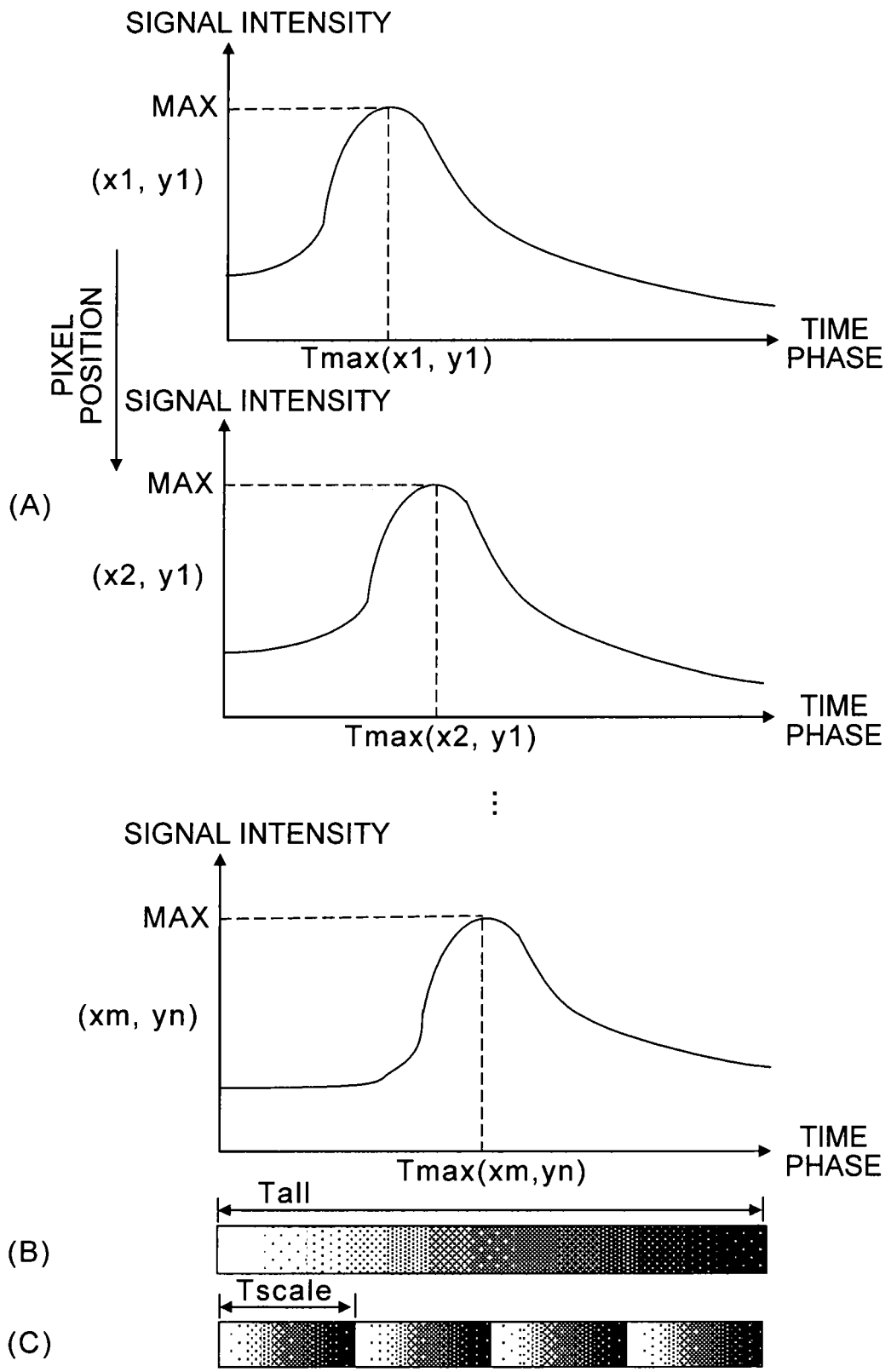
FIG. 3 shows the first example of color scale assigned to time phases corresponding to the maximum values of concentration profiles of a contrast agent.

FIG. 3 shows the first example of color scale assigned to time phases corresponding to the maximum values of concentration profiles of a contrast agent.

(A) of FIG. 3 shows concentration profiles of a contrast agent at two dimensional positions (xi, yj) (i=1, 2, 3, . . . , m; j=1, 2, 3, . . . , n) and arrival time phases Tmax (xi, yj) of the contrast agent specified based on the maximum values MAXs of the concentration profiles. The contrast agent arrives at a position, which is close to an injection position of the contrast agent, relatively early. Therefore, specified time phases are also relatively early. On the other hand, the contrast agent arrives at a position, which is away from the injection position of the contrast agent, relatively late. Therefore, specified time phases are also relatively late.

(B) of FIG. 3 shows an example of color scale assigned to the specified time phases as shown in (A) of FIG. 3. As shown in (B) of FIG. 3, a color scale can be generated by assigning a change in color pixel value, consisting of R value, B value and G value, to a period Tall from the initial time to the ending time of time changes in concentrations of a contrast agent obtained as the concentration profiles. That is, a color scale can be generated by assigning a continuous color phase change to the period Tall from the initial time to the ending time of time change in concentration of a contrast agent.

According to the color scale as shown in (B) of FIG. 3, a two dimensional time phase map showing arrival time phases of a contrast agent can be color coded. Then, parametric image data in which blood vessels have been depicted by different colors according to arrival time phases of a contrast agent can be generated.

However, when a difference in the arrival time phases Tmax (xi, yj) of a contrast agent between the pixel positions (xi, yj) is small relatively to a range of the color scale, as shown in (A) of FIG. 3, a difference in color between the pixel positions (xi, yj) becomes also small. Therefore, it may become difficult to distinguish blood vessels by the difference in color.

In particular, when X-ray imaging is performed for the purpose of diagnosing a dural arteriovenous fistula or a cerebral arteriovenous malformation, it is important to observe blood flows between arteries and veins. Therefore, it is often necessary to distinguish blood vessels having small differences in arrival times of a contrast agent.

Thus, a color scale can be changed in the color scale adjustment part 24 so that even blood vessels between which differences in arrival times of a contrast agent are small can be distinguished as differences in color. (C) of FIG. 3 shows an example of generating a color scale by assigning the continuous color phase change multiple times to the period Tall, from the initial time to the ending time of time changes in concentrations of a contrast agent, as changes in pixel values. That is, a color scale in which a continuous color phase change is repeated periodically can be generated.

The color scale as shown in (C) of FIG. 3 can be generated by designating a pixel value corresponding to the initial time phase of concentration profiles, a period Tscale of a change in pixel value, and the initial pixel value in the period Tscale, with an operation of the console 5. Thereby, it is possible to generate a color scale in which the change in pixel value is repeated according to the designated initial pixel value and the designated period Tscale. Then, the colors can be arranged in each period Tscale similarly to the color scheme as shown in (B) of FIG. 3. Specifically, a color scale in which a color phase showing the maximum value changes among red, green and blue in one period Tscale can be generated.

Figure 4:
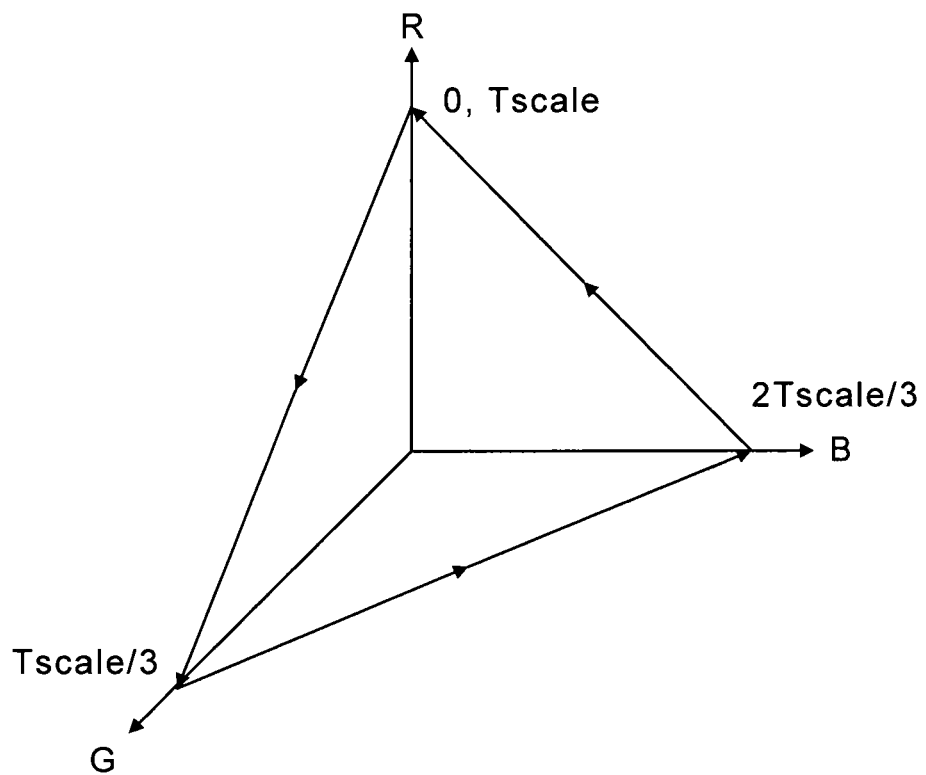
FIG. 4 shows an example of color scheme in the color scale shown in (C) of FIG. 3.

FIG. 4 shows an example of color scheme in the color scale shown in (C) of FIG. 3.

The three orthogonal axes in FIG. 4 represent R values, G values, and B values, respectively. The R value, G value, and B value corresponding to each time phase in the period Tscale can be determined along the sides of the color triangle, whose vertexes are the maximum value of the R values, the maximum value of the G values, and the maximum value of the B values, as shown in FIG. 4. Specifically, the colors can be arranged so that the G value and the B value become zero and the R value becomes the maximum value when the relative time is zero or Tscale, the R value and the B value become zero and the G value becomes the maximum value when the relative time is Tscale/3, and the R value and the G value become zero and the B value becomes the maximum value when the relative time is 2Tscale/3.

When such a color scheme is performed, parametric image data can be generated so that the color changes from red to blue through green, and then returns to red again according to the time phase. Note that, the colors between red, green, and blue can be assigned to time phases so that the R value, the G value, and the B value change linearly, for example. Alternatively, the R values, the G values, and the B values may also be assigned to time phases so that the angle of a line segment, which connects the center of the color triangle with a point on the sides, changes linearly.

When parametric image data are generated according to a color scale generated by such a color scheme, blood vessels can be distinguished as a difference in colors even when differences in arrival times of a contrast agent are small. That is, arrival times of a contrast agent can be understood in detail.

Note that, the most visible color is red. Therefore, as exemplified in FIG. 4, setting the color of an initial time phase, which corresponds to the earliest arrival time of a contrast agent, to red leads to an improvement of visibility. That is, it is effective to set a color value, corresponding to the initial time phase of a color scale, to the maximum value of the R value. Moreover, as another example, it is also useful to adjust the initial time phase so that a focused time phase becomes red.

Figure 5:
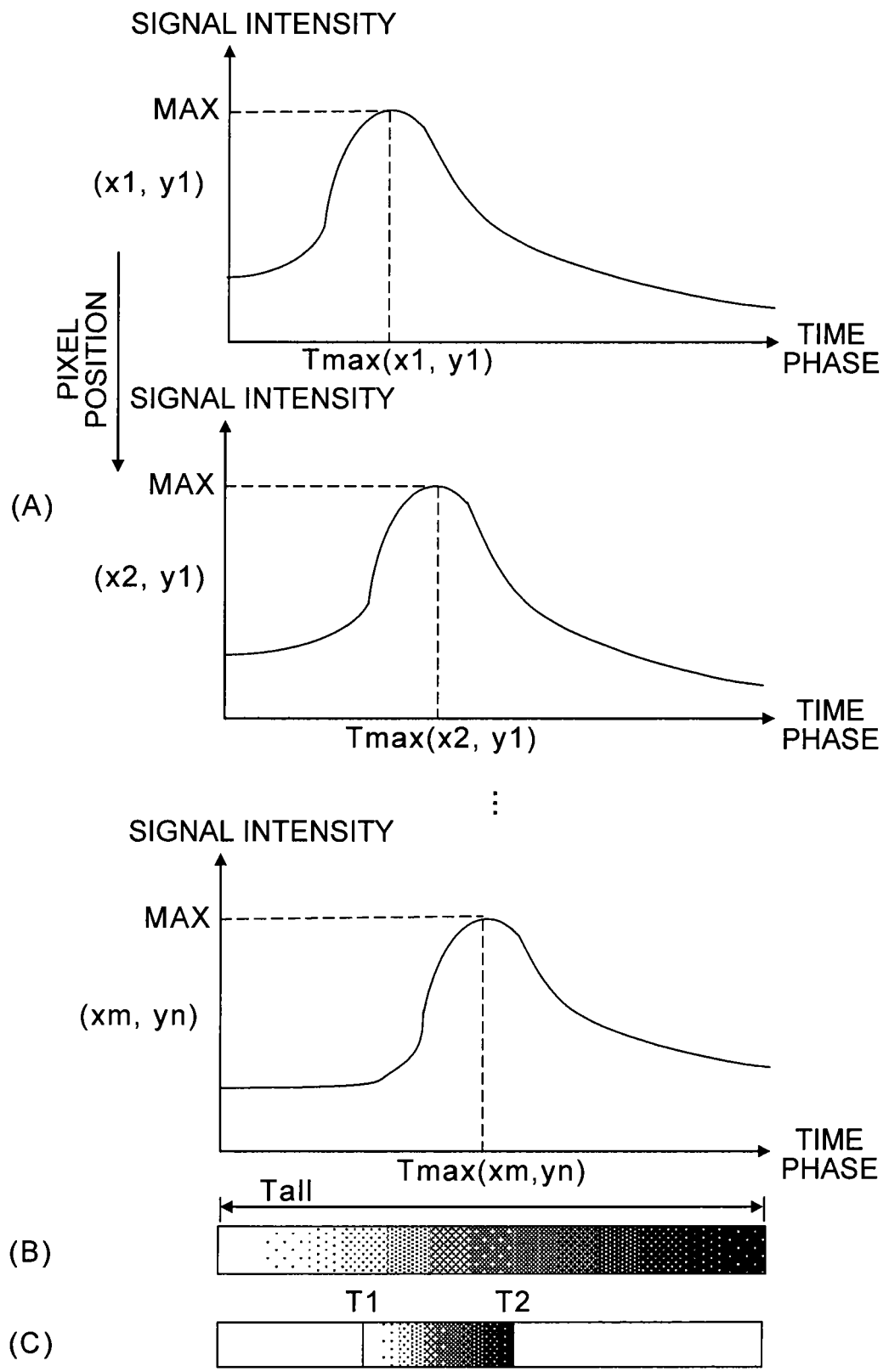
FIG. 5 shows the second example of color scale assigned to time phases corresponding to the maximum values of concentration profiles of a contrast agent.

FIG. 5 shows the second example of color scale assigned to time phases corresponding to the maximum values of concentration profiles of a contrast agent.

(A) of FIG. 5 shows concentration profiles of a contrast agent at two dimensional positions (xi, yj) (i=1, 2, 3, ..., m; j=1, 2, 3, ..., n) and arrival time phases Tmax (xi, yj) of the contrast agent specified based on the maximum values MAXs of the concentration profiles, similarly to (A) of FIG. 3.

Then, the color scale as shown in (B) of FIG. 5, in which a change in color pixel value is assigned to the period Tall from the initial time to the ending time of time changes in concentrations of a contrast agent, can be changed into the color scale shown in (C) of FIG. 5. The color scale shown in (C) of FIG. 5 is generated by assigning the continuous color phase change, as a change in pixel value, to a designated period. The period to which the change in pixel value is assigned can be determined by designating a starting time phase T1 and an ending time phase T2. The starting time phase T1 and the ending time phase T2 can be designated by selecting corresponding images respectively from time series X-ray contrast images or time series DSA images.

Figure 6:
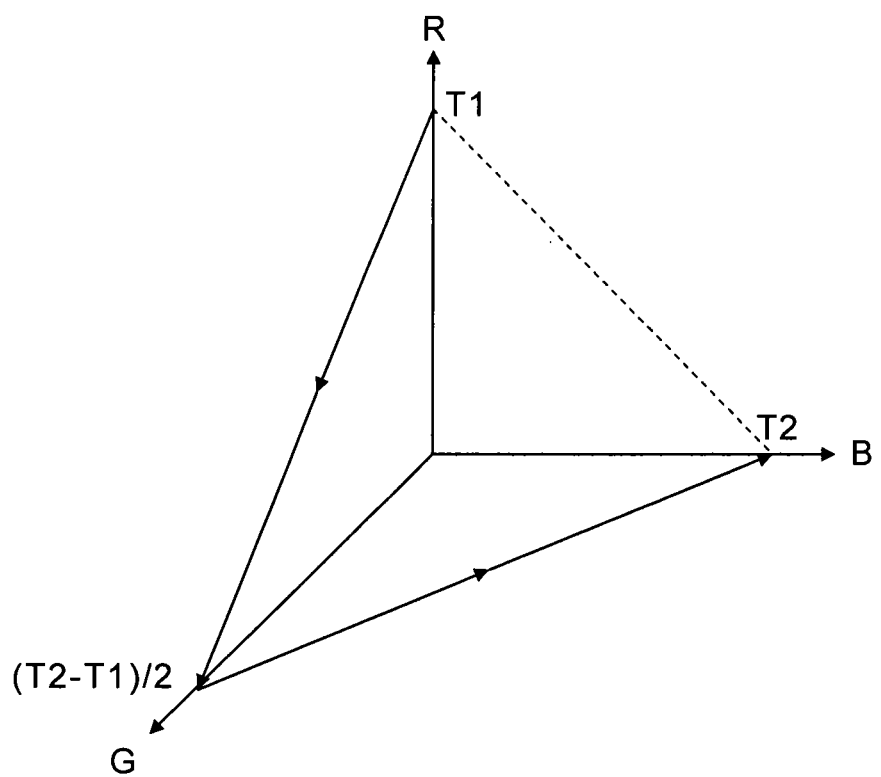
FIG. 6 shows an example of color scheme in the color scale shown in (C) of FIG. 5.

FIG. 6 shows an example of color scheme in the color scale shown in (C) of FIG. 5.

The three orthogonal axes in FIG. 6 represent R values, G values and B values, respectively. Similarly to FIG. 4, the R value, G value and B value corresponding to each time phase within a designated period can be determined along the sides of the color triangle. Specifically, the colors can be arranged so that the G value and the B value become zero and the R value becomes the maximum value at the starting time phase T1, the R value and the B value become zero and the G value becomes the maximum value at the middle time phase between the starting time phase T1 and the ending time phase T2, and the R value and the G value become zero and the B value becomes the maximum value at the ending time phase T2, similarly to an example shown in FIG. 4.

When the colors are arranged as shown in FIG. 6, a color scale in which a color phase showing the maximum value changes among red, green and blue between the starting time phase T1 and the ending time phase T2 can be generated. That is, a color scale whose color changes from red to blue through green within a designated period can be generated.

With regard to time phase other than a designated period, a pixel value pattern different from a change in pixel value in the designated period can be assigned. For example, color phases may be changed between the inside and the outside of the designated period. As a more specific example, a color scale can be generated so that the color phase changes from white to red at the time phases before the starting time phase T1 while the color phase changes from blue to white at the time phases after the ending time phase T2.

Furthermore, a transmittance different from that in a designated period can also be assigned to time phase other than the designated period. As a specific example, a color scale can be generated so that the transmittance changes from the maximum value to zero at the time phases before the starting time phase T1 while the transmittance changes from zero to the maximum value at the time phases after the ending time phase T2. That is, the transmittance may be changed in a predetermined range, in time phases outside the designated period. In this case, it is not necessary to change color values, such as R value and B value, outside the designated period.

As described above, at least one of pixel values, including R value, G value and B value, and the transmittance, in the time phase ranges outside the designated period can be changed from those within the designated period.

Each color scale after the change as shown in (C) of FIG. 3 and (C) of FIG. 5 can also be changed dynamically. Specifically, plural color scales can be generated by changing at least one of a phase and a period of change in pixel value of a color scale as shown in (C) of FIG. 3 or (C) of FIG. 5. Changing a phase of change in pixel value corresponds to shifting a color scale in the time phase direction. Meanwhile, changing a period of change in pixel value corresponds to expanding or contracting a color scale in the time phase direction.

When the color coding of parametric image data is performed using color scales having different color schemes as described above, frames of parametric image data corresponding to the color scales are generated. Thus, it becomes possible to display the frames of generated parametric image data in the color scale direction as a moving image. That is, blood vessel image data can be generated as a moving image according to plural color scales generated by changing at least one of a phase and a period of change in pixel value. Therefore, it becomes possible to understand flows of a contrast agent and blood more easily. In particular, human eyes have high visibility to red. Therefore, generating a moving image in which red moves during a focused period from the starting time phase T1 to the ending time phase T2 allows easy understanding of a blood flow dynamic state in a focused region.

As a specific example, when colors are changed in the designated period as shown in (C) of FIG. 5, a color corresponding to each time phase can be changed in time. In this case, a color changes among red, green and blue even at a same time phase. With regard to the outside of the designated period, colors at the starting time phase T1 and the ending time phase T2 can be gradually changed into white respectively, or the transmittances of colors can be changed.

Meanwhile, in the case of the color scale in which color values have been changed periodically, plural color scales can be generated by gradually changing the initial color value in each period.

The color values including the R value, the G value and the B value can also be changed into values other than the maximum values. Specifically, when parametric image data are generated by the above-mentioned color scale, a brightness value at each pixel, at which a value of a concentration profile of a contrast agent has not become zero by low-pass filtering processing or the like, becomes the maximum value. That is, a brightness value at each pixel at which a contrast agent arrived becomes the maximum value, regardless of a concentration of the contrast agent.

Thus, brightness values of parametric image data can be changed so that concentrations of a contrast agent can be understood. In other words, parametric image data having brightness values according to concentrations of a contrast agent at a specific condition, such as the maximum values, can be generated as blood vessel image data.

Specifically, when the maximum R value, G value and B value before the change in brightness values are $R_0$, $G_0$ and $B_0$, respectively, the R value, G value and B value after the change in brightness values can be determined by multiplying each of the values $R_0$, $G_0$ and $B_0$ by a coefficient k, as shown in expression (1).

$$(R, G, B) = (kR_0, kG_0, kB_0) \quad (1)$$

In expression (1), the coefficient k is set to a value not less than zero and not more than one, corresponding to a concentration of a contrast agent. For example, the coefficient k can be determined by expression (2).

$$k=P(x,y)/P_0 \qquad (2)$$

wherein P(x, y) represents a value, corresponding to a specific condition such as the maximum value, of a concentration profile of a contrast agent at a position (x, y), obtained as an image signal value of X-ray contrast image data or DSA image data, and $P_0$ represents a constant.

When the coefficient k is set by expression (2), the coefficient k becomes a value proportional to the value P(x, y) of a concentration profile of a contrast agent. Therefore, the brightness values (R, G, B) of parametric image data can also be brightness values each proportional to the value P(x, y) of a concentration profile of a contrast agent. Furthermore, brightness values at a pixel where a concentration of a contrast agent is a noise level and brightness values at a pixel where noises have actually occurred can be made small enough.

The constant $P_0$ can be set to the maximum value of the value P(x, y) of a concentration profile of a contrast agent in spatial directions, or an arbitrary value which has been determined empirically. Note that, when the constant $P_0$ is set to a value smaller than the maximum value of the value P(x, y) of a concentration profile of a contrast agent, the coefficient k may become a value larger than one, by the calculation of expression (2). In such a case, the coefficient k has only to be set to one.

Then, when a pixel value adjusted by expression (1) is assigned to each pixel position (x, y), parametric image data in which blood vessels have been depicted in colors and brightness according to arrival time phases and concentrations of a contrast agent can be generated. Note that, the adjustment of brightness values shown in expression (1) can be performed at the time of the color coding in the color coding part 23.

The parametric image data generated in the parametric image generation part 21 as described above can be displayed on the display 14, similarly to X-ray contrast image data or DSA image data. Furthermore, the parametric image data can be stored in the image memory 16 as necessary.

Figure 7:
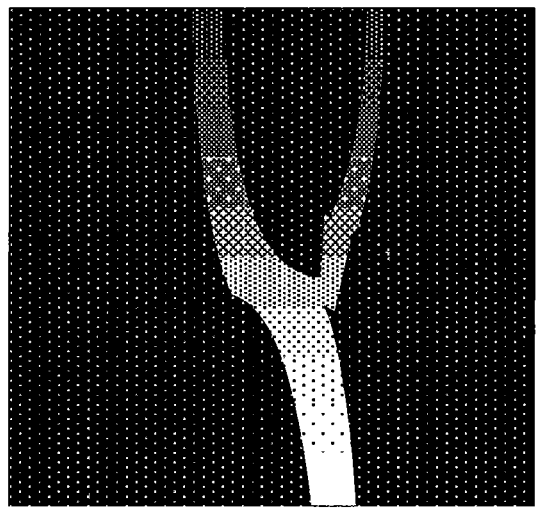
FIG. 7 shows an example of parametric image generated in the parametric image generation part shown in FIG. 1.

FIG. 7 shows an example of parametric image generated in the parametric image generation part 21 shown in FIG. 1.

In a parametric image, blood vessels into which a contrast agent has been injected are displayed in color while brightness values become zero in regions without the contrast agent, as shown in FIG. 7. Furthermore, the blood vessels are depicted as a region or regions where colors change according to arrival times of the contrast agent. Therefore, how blood and the contrast agent flow can be observed by colors.

A parametric image as shown in FIG. 7 can be acquired repeatedly at different times and dates, in order to observe temporal changes of an object O. For example, when a parametric image is generated before and after treatment of an object O, treatment progress of the object O can be observed.

That is, the first blood vessel image data and the second blood vessel image data can be obtained by performing image generation processing, for generating parametric image data which are time phase image data, multiple times based on X-ray contrast image data sets acquired at different times. Then, the first blood vessel image and the second blood vessel image can be displayed so that comparative interpretation can be performed.

When the first blood vessel image data and the second blood vessel image data have been color coded under different conditions, corresponding time phases are to be displayed in different colors. Therefore, comparative interpretation of blood vessel images may become difficult.

Thus, the color synchronization display processing part 25 of the parametric image generation part 21 is configured to determine or correct pixel values of at least one of the first blood vessel image data and the second blood vessel image data so that pixel values of corresponding time phases between the first blood vessel image data and the second blood vessel image data coincide, by giving instruction information to the color coding part 23 and the color scale adjustment part 24.

When the first blood vessel image data have been obtained in the past and the second blood vessel image data are newly generated, for example, pixel values corresponding to time phases of the second blood vessel image data can be determined in conformity with pixel values corresponding to time phases of the first blood vessel image data. Alternatively, when both the first blood vessel image data and the second blood vessel image data have already been generated, pixel values of at least one of the first blood vessel image data and the second blood vessel image data can be corrected so that pixel values of corresponding time phases coincide. Hereinafter, a case where the first blood vessel image data have been generated as past image data before the second blood vessel image data will be described.

At the time of or after generating the second blood vessel image data, the past first blood vessel image data can be manually selected by operating the console 5. Specifically, the image memory 16 can be searched, and parametric image data acquired from the same direction under nearly same conditions in the past can be selected as the first blood vessel image data, by operating the console 5. Alternatively, past time series X-ray contrast image data or DSA image data may be selected as original data of parametric image data.

As a matter of course, the color synchronization display processing part 25 may also have a function to automatically select the past first blood vessel image data. For example, the color synchronization display processing part 25 can search past examination information on the same object O, and automatically obtain parametric image data, time series DSA image data, or time series X-ray contrast image data acquired by the same imaging protocol or at the same imaging angle and imaging position.

There are a variety of methods for making relationships between time phases and color pixel values coincide between the first blood vessel image data and the second blood vessel image data. When relationships between time phases and pixel values are to be able to be made coincide in arbitrarily selected one of different methods, color synchronization modes depending on the methods can be set.

Figure 8:
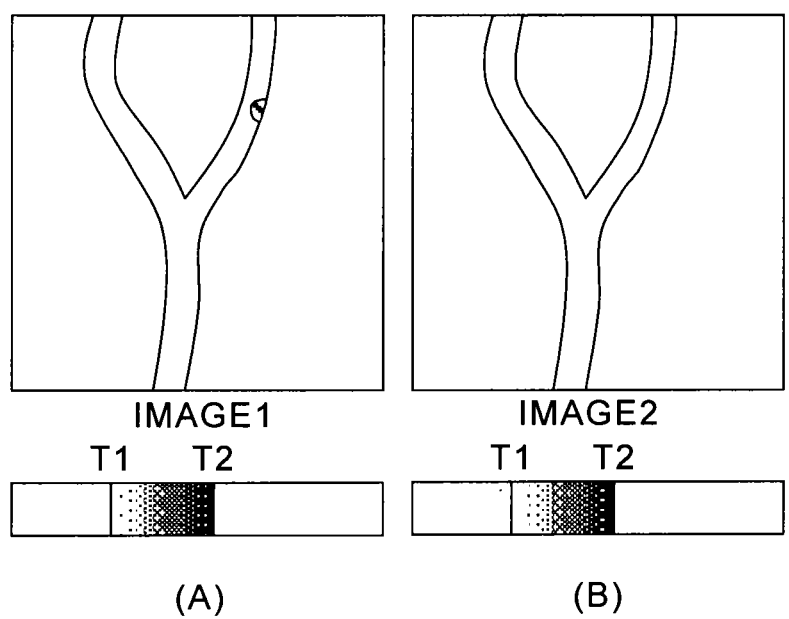
FIG. 8 shows an example of determining or correcting pixel values of the second blood vessel image data according to a color scale used for generating the past first blood vessel image data.

FIG. 8 shows an example of determining or correcting pixel values of the second blood vessel image data according to a color scale used for generating the past first blood vessel image data.

(A) of FIG. 8 shows an example of the first blood vessel image data acquired in the past and a color scale used for generating the first blood vessel image data. (B) of FIG. 8 shows an example of the newly acquired second blood vessel image data and a color scale used for generating the second blood vessel image data.

As shown in FIG. 8, the second blood vessel image data can be color-coded according to the same color scale as the color scale used for generating the past first blood vessel image data. In the example shown in FIG. 8, a color scale in which a continuous change in color phase has been assigned to a designated period from the starting time phase T1 to the ending time phase T2, as shown in (C) of FIG. 5, has been used. As a matter of course, when a color scale having a periodic color phase change as shown in (C) of FIG. 3 or a monotonic color scale as shown in (B) of FIG. 3 and (B) of FIG. 5 has been used for generating the first blood vessel image data, the second blood vessel image data can be generated or corrected using a color scale having the same color phase change as that of the color scale used for generating the first blood vessel image data.

That is, the color synchronization display processing part 25 can obtain information to specify a color scale used for generating the first blood vessel image data, and determine or correct pixel values of the second blood vessel image data, according to the same color scale as the color scale used for generating the first blood vessel image data, based on the obtained information. The information to specify a color scale used for generating the first blood vessel image data can be obtained from incidental information on the first blood vessel image data. Conversely, information to specify a color scale used for generating the first blood vessel image data can be stored in the image memory 16, together with the first blood vessel image data, as incidental information on the first blood vessel image data. Thereby, a color scale used for generating the first blood vessel image data can be specified at the time of generating the second blood vessel image data.

When the first blood vessel image data and the second blood vessel image data generated using an identical color scale as described above are displayed in parallel on the display 14, corresponding time phases can be displayed in a same color by very simple display processing. Even when not less than three blood vessel image data sets exist, relationships between time phases and colors in blood vessel image data sets other than a selected one blood vessel image data set can be adjusted so that the relationship between time phases and colors of each of the other blood vessel image data sets coincide with relationship between time phases and colors in the selected one blood vessel image data set.

However, when X-ray imaging is performed at different times and dates, such as before and after a treatment, time series X-ray contrast image data sets are not necessarily acquired at the same time from the start time of contrast agent injection. Furthermore, an arrival time of a contrast agent to a same position also changes when a difference in position of a catheter for injecting the contrast agent is large between imaging times and dates. Therefore, even at a same position, arrival time phases of a contrast agent may change between the first blood vessel image data and the second blood vessel image data, due to a factor other than the treatment. In this case, even when the same color scale is used, the same position is displayed in different colors between the first blood vessel image data and the second blood vessel image data.

Thus, a correction to make time phases correspond to each other between the first blood vessel image data and the second blood vessel image data can also be performed. Thereby, a same position can be displayed in a same color between the first blood vessel image data and the second blood vessel image data.

To correct time phases in order to make colors coincide at each same position is equivalent to correct color schemes of color scales, without changing the time phases. Therefore, colors at each unchanged position can be made coincide between the first blood vessel image data and the second blood vessel image data, by correcting at least one of time phases and pixel values of color scales. A correction of time phases can be performed in the color coding part 23. Meanwhile, a correction of color pixel values on a color scale can be performed in the color scale adjustment part 24.

Figure 9:
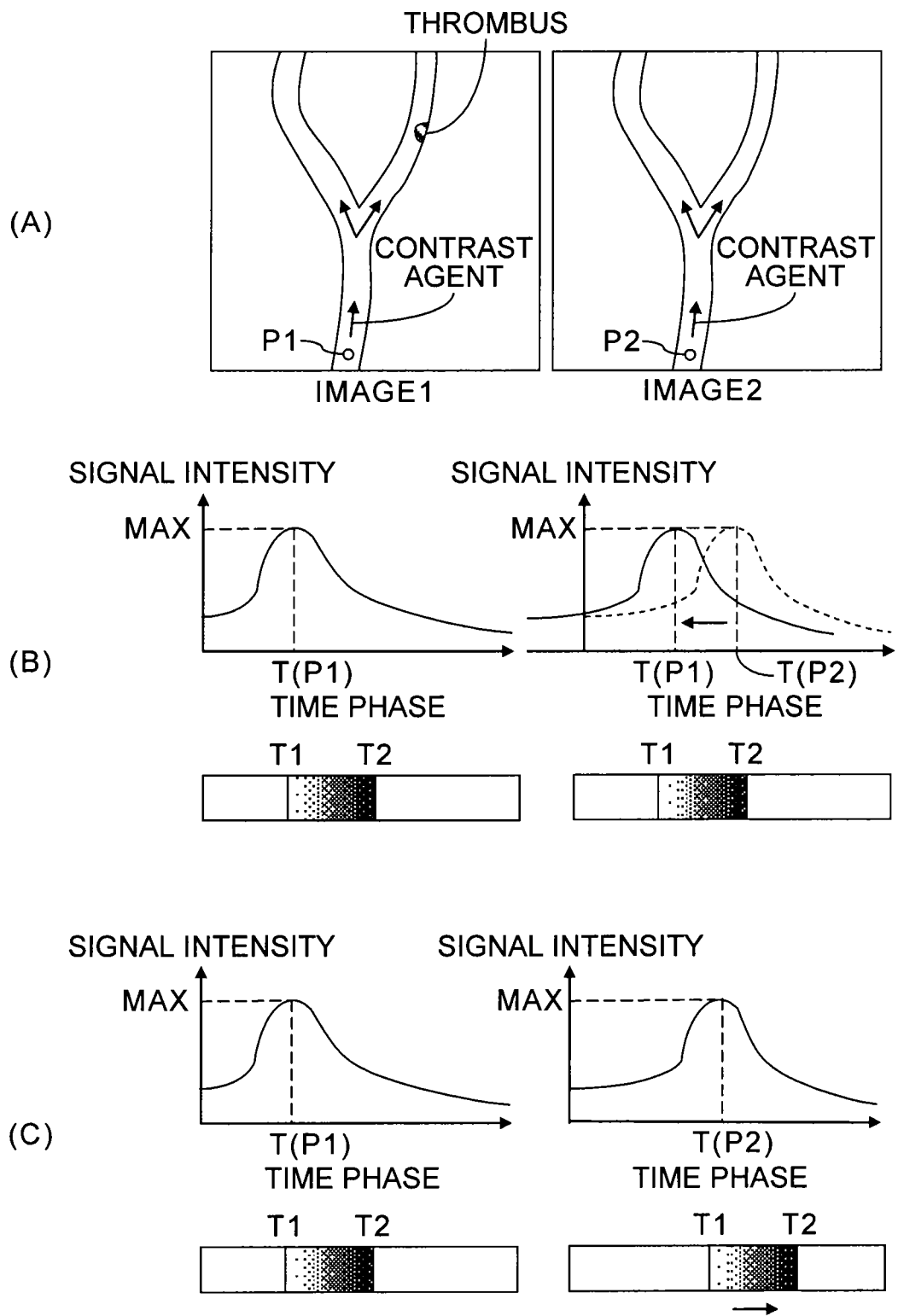
FIG. 9 shows an example of making a color at a designated position or colors in a designated region coincide between the first blood vessel image data and the second blood vessel image data.

FIG. 9 shows an example of making a color at a designated position or colors in a designated region coincide between the first blood vessel image data and the second blood vessel image data.

(A) of FIG. 9 shows an example of displaying the first blood vessel image before a treatment, on which a thrombus has been depicted, and the second blood vessel image after the treatment, from which the thrombus has been removed, in parallel. As shown in (A) of FIG. 9, the first position P1 can be designated on the first blood vessel image data before the treatment, which have been acquired in the past, by operating the console 5, for example. If blood flow at the first position P1 does not change before and after the treatment, it is desirable to display the first position P1 on the first blood vessel image and the second position P2, corresponding to the first position P1, on the second blood vessel image in a same color.

Thus, pixel values of at least one of the first blood vessel image data and the second blood vessel image data can be corrected so that the first time phase T(P1) at the first position P1 designated on the first blood vessel image data and the second time phase T(P2) at the second position P2, corresponding to the first position P1, on the second blood vessel image data become time phases corresponding to each other, to which a same pixel value should be assigned.

Specifically, one or both of time phases and color schemes of color scales corresponding to the time phases can be corrected as described above. In the case of correcting only time phases, at least one of the first time phase T(P1) and the second time phase T(P2) is corrected so that the time phase at the first position P1 coincides with the time phase at the second position P2. Meanwhile, in the case of changing only color scales, the color scales are adjusted so that a color corresponding to the first time phase T(P1) coincides with a color corresponding to the second time phase T(P2).

(B) of FIG. 9 shows concentration profiles of a contrast agent and corresponding color scales in case where a correction to make the second time phase T(P2) at the second position P2 of the second blood vessel image data coincide with the first time phase T(P1) at the first position P1 of the first blood vessel image data has been performed based on the identical color scale between the first blood vessel image data and the second blood vessel image data. The concentration profile of a contrast agent at the second position P2 of the second blood vessel image data shown by the dotted line in (B) of FIG. 9 can be corrected to a concentration profile of the contrast agent shown by the solid line in (B) of FIG. 9. As shown in (B) of FIG. 9, a correction of a time phase at a certain position visually corresponds to a parallel translation of a concentration profile of a contrast agent. Therefore, a color at the second position P2 can be made coincide with a color at the first position P1.

Meanwhile, (C) of FIG. 9 shows an example case of correcting only a color scale, instead of correcting time phases. In this case, the color scale corresponding to the second blood vessel image data has only to be corrected so that the pixel value corresponding to the second time phase T(P2) coincides with the pixel value corresponding to the first time phase T(P1). As shown in (C) of FIG. 9, a correction of a color scale visually corresponds to a parallel translation of a portion, having a continuous color phase change, of the color scale.

Note that, a region may be designated instead of a position. In that case, what is necessary is to change time phases or a color scheme of a color scale so that pixel values representing regions coincide with each other. The second position P2 or the second region corresponding to the designated first position P1 or the designated first region respectively can be automatically detected based on coordinate information, or can also be manually designated by operating the console 5.

Methods of automatically identifying the second position P2 or the second region, corresponding to the manually designated first position P1 or the manually designated region respectively, include a method by extracting contours of blood vessels depicted in color. Specifically, contours of blood vessels in a rectangular region, which centers on the first position P1 and of which one side has a length $\Delta$, can be extracted from the first blood vessel image data by image processing, such as edge extraction processing, and the rectangular region including the extracted contours of the blood vessels can be searched in the second blood vessel image data. Then, the center position of the rectangular region, of which one side has the length $\Delta$, detected in the second blood vessel image data can be identified as the second position P2. In the case of automatically identifying the second region corresponding to the first region, the second region can also be identified in a similar method when the first region is small. Meanwhile, when the first region is large, the first region can be divided into unit regions, and the similar method can be applied to every unit region.

In the examples shown in (B) and (C) of FIG. 9, pixel values corresponding to time phases at which the signal intensities showing concentrations of a contrast agent become the maximum values have been made to coincide with each other between the first blood vessel image data and the second blood vessel image data. However, a time phase shift amount between concentration profiles can be obtained by another method. Specifically, a time phase difference between concentration profiles of a contrast agent can be obtained as a time phase shift amount which should be corrected, instead of setting a time phase difference between the maximum values of the concentration profiles as the time phase shift amount which should be corrected.

Figure 10:
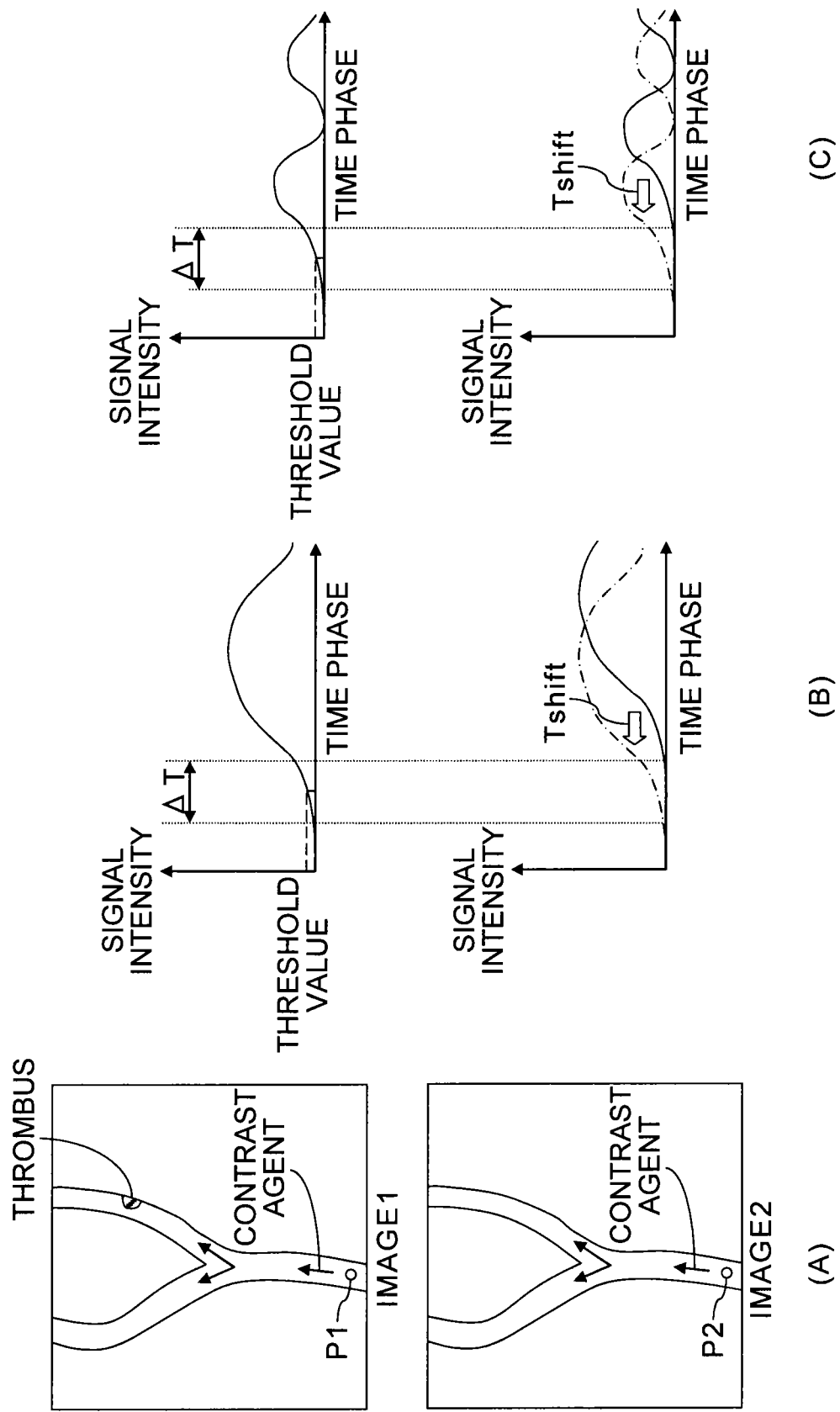
FIG. 10 shows an example of obtaining a time phase difference between concentration profiles of a contrast agent, corresponding to the first position P1 of the first blood vessel image data and the second position P2 of the second blood vessel image data, using parts of the concentration profiles.

FIG. 10 shows an example of obtaining a time phase difference between concentration profiles of a contrast agent, corresponding to the first position P1 of the first blood vessel image data and the second position P2 of the second blood vessel image data, using parts of the concentration profiles.

In (A) of FIG. 10, the first blood vessel image data, on which the first position P1 has been designated, and the second blood vessel image data, on which the second position P2 corresponding to the first position P1 has been specified, are displayed in parallel, similarly to (A) of FIG. 9.

(B) of FIG. 10 shows the first example of comparing a concentration profile of a contrast agent at the first position P1 of the first blood vessel image data with a concentration profile of the contrast agent at the second position P2 of the second blood vessel image data. As shown in (B) of FIG. 10, a concentration profile of the contrast agent, at the first position P1, during an arbitrary time phase range $\Delta T$ can be extracted by setting a threshold value in signal intensity of the concentration profile of the contrast agent at the first position P1.

For example, a predetermined range centering on a time phase, at which the signal intensity of the concentration profile has exceeded the threshold value, can be determined as the time phase range $\Delta T$. The threshold value can be previously determined as a value which can be considered to represent that the contrast agent has arrived, for example.

Meanwhile, the concentration profile of the contrast agent at the second position P2 can be shifted in the time phase direction using a shift amount as a parameter, and a shift amount when a cross-correlation coefficient in the extracted time phase range $\Delta T$ becomes the maximum value can be obtained. When the above-mentioned optimization operation is performed, a shift amount Tshift of the concentration profile of the contrast agent at the second position P2 can be calculated as a time phase difference between the two concentration profiles.

Note that, an optimization operation may also be performed using an index, such as the least square error, showing a deviation amount, instead of a cross-correlation coefficient. Therefore, depending on an index, a time phase difference between the two concentration profiles is occasionally calculated by an optimization operation which minimizes the index.

(C) of FIG. 10 shows the second example of comparing a concentration profile of the contrast agent at the first position P1 with a concentration profile of the contrast agent at the second position P2. When a blood flow is fast with respect to an injection amount of the contrast agent per unit time, the contrast agent may shuttle under an influence of heartbeat. In such a case, a concentration profile of the contrast agent may become a wavy curve having a plurality of the local maximum values as shown in (C) of FIG. 10.

When an optimization operation, which maximizes a cross-correlation coefficient, is performed to the wavy concentration profile as shown in (C) of FIG. 10, the cross-correlation coefficient increases or decreases depending on a shift amount of the concentration profile. Therefore, an inappropriate shift amount of time phase may be obtained as the optimal solution.

Thus, a time phase range $\Delta T$ can be determined based on a time phase at which the signal intensities of the concentration profile of the contrast agent at the first position P1 have exceeded a threshold value first, and then a shift amount Tshift in the time phase direction corresponding to the first peak of a cross-correlation coefficient can be obtained as the optimal solution. Thereby, an appropriate time phase difference between the two concentration profiles can be calculated.

By such a calculation method of a time phase difference with an optimization operation, a calculation of a time phase difference and a correction of time phases can be performed more accurately. As a matter of course, a correction of the color scale side as shown in (C) of FIG. 9 may also be performed according to an obtained time phase difference.

Then, the above-mentioned correction of one or both of a time phase and a color scale can be performed for all pixel positions. Thereby, colors in the first blood vessel image data can correspond to those in the second blood vessel image data. Specifically, the same unchanged part can be displayed in a same color on the first blood vessel image and the second blood vessel image even when positions of catheters for injecting the contrast agent differ from each other or timing of X-ray contrast imaging differs. Accordingly, comparative interpretation of the first blood vessel image and the second blood vessel image becomes easy.

Note that, when velocities of blood flows differ from each other between a time of acquiring the first blood vessel image data and a time of acquiring the second blood vessel image data, due to a difference in heart rate of the object O or the like, a flow velocity of the contrast agent changes. In that case, an arrival time phase of the contrast agent at a position far from an injection position of the contrast agent changes depending on a difference in flow velocity of the contrast agent. Therefore, a same unchanged part may not be displayed in a same color between the first blood vessel image and the second blood vessel image even when the correction as shown in FIG. 9 has been performed. In such a case, plural positions or regions can be designated as targets of which colors should be made to coincide.

Figure 11:
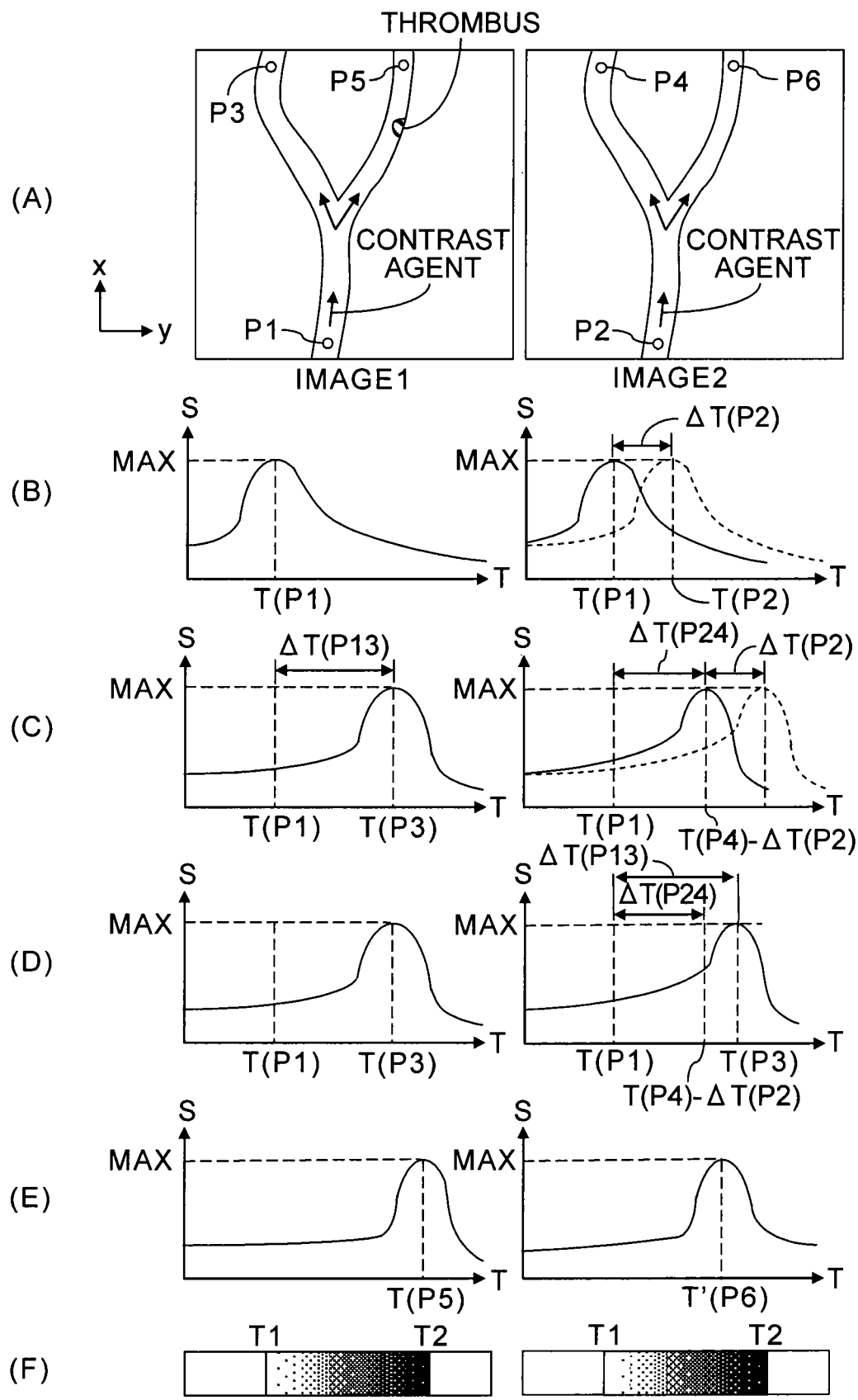
FIG. 11 shows an example of making colors at designated two positions or in designated two regions coincide between the first blood vessel image data and the second blood vessel image data.

FIG. 11 shows an example of making colors at designated two positions or in designated two regions coincide between the first blood vessel image data and the second blood vessel image data.

(A) of FIG. 11 shows an example of displaying the first blood vessel image before a treatment, on which a thrombus has been depicted, and the second blood vessel image after the treatment, from which the thrombus has been removed, in parallel. For example, the third position P3 other than the first position P1 can be designated on the first blood vessel image data before the treatment, which have been acquired in the past, by operating the console 5 as shown in (A) of FIG. 11.

When blood flows at both the first position P1 and the third position P3 do not change before and after the treatment, it is desirable to display not only the first position P1 on the first blood vessel image and the second position P2, corresponding to the first position P1, on the second blood vessel image, but also the third position P3 on the first blood vessel image and the fourth position P4, corresponding to the third position P3, on the second blood vessel image in same colors, respectively.

However, when a velocity of blood flow at the time of acquiring the first blood vessel image differs from that of acquiring the second blood vessel image, a time phase at which the contrast agent has arrived at the third position P3 do not coincide with a time phase at which the contrast agent has arrived at the fourth position P4 though a time phase at which the contrast agent has arrived at the first position P1 coincides with a time phase at which the contrast agent has arrived at the second position P2.

Thus, pixel values of at least one of the first blood vessel image data and the second blood vessel image data can be corrected so that not only the time phases at the first position P1 and the second position P2 become corresponding time phases but the third time phase T(P3) at the third position P3 further designated on the first blood vessel image data and the fourth time phase T(P4) at the fourth position P4, corresponding to the third position P3, on the second blood vessel image data become other corresponding time phases. Similarly to the second position P2, the fourth position P4 can also be manually designated or automatically detected. In this case, pixel values can be corrected with interpolation processing so that time phases of positions between the first position P1 and the third position P3 correspond to time phases of positions between the second position P2 and the fourth position P4.

The target of the interpolation processing is at least one of time phases and phases of a continuous color phase change in a color scale. To use a linear interpolation as the interpolation processing leads to simplification of the processing.

In (B), (C), (D) and (E) of FIG. 11, each vertical axis shows signal intensities S corresponding to concentrations of a contrast agent while each horizontal axis shows time phases T. (F) of FIG. 11 shows color scales used for displaying the first blood vessel image data and the second blood vessel image data.

(B) to (E) of FIG. 11 show changes of concentration profiles of a contrast agent in the case of using an identical color scale between the first blood vessel image data and the second blood vessel image data, and correcting time phases of the second blood vessel image data with a linear interpolation of the time phases. The concentration profiles on the left side and the color scale on the left side of FIG. 11 correspond to the first blood vessel image data while the concentration profiles on the right side and the color scale on the right side in FIG. 11 correspond to the second blood vessel image data.

Firstly, a correction to shift the time phases T at all positions of the second blood vessel image data, in the time phase direction by a shift amount $\Delta T(P2)$ is performed as the first correction so that the second time phase T(P2) at the second position P2 of the second blood vessel image data becomes the first time phase T(P1) at the first position P1 of the first blood vessel image data. This visually corresponds to shifting the concentration profiles of the contrast agent, at the respective positions of the second blood vessel image data, in the time phase direction by the shift amount $\Delta T(P2)$.

In (B) of FIG. 11, a profile at the first position P1 of the first blood vessel image data is shown on the left side while a profile at the second position P2 of the second blood vessel image data and a profile after the first correction of the profile at the second position P2 are shown on the right side as the dotted line and the solid line, respectively. Similarly, in (C) of FIG. 11, a profile at the third position P3 of the first blood vessel image data is shown on the left side while a profile at the fourth position P4 of the second blood vessel image data and a profile after the first correction of the profile at the fourth position P4 are shown on the right side as the dotted line and the solid line, respectively. Here, $\Delta T(P13)$ shows a time difference between T(P1) and T(P3), and $\Delta T(P24)$ shows a time difference between T(P1) and a result of the first correction applied to T(P4).

$\Delta T(P13)$ is supposed to coincide with $\Delta T(P24)$ when there is no factor resulting from a state of a blood vessel, such as a stenosis. When there is no factor as described above, it can be considered that the difference between $\Delta T(P13)$ and $\Delta T(P24)$ has occurred due to a change in velocity of a blood flow. Therefore, an expansion and contraction correction is performed as the second correction by multiplying T'(P4) (=T(P4)−$\Delta T(P2)$) by $\Delta T(P13)/\Delta T(P24)$ on the basis of T(P1). The result of applying the second correction to the profile at the fourth position P4 of the second blood vessel image data is shown on the right side of (D) of FIG. 11.

In summary, a profile at an arbitrary position of the second blood vessel image data is corrected by expression (3). That is, time phase data T2 of the second blood vessel image data are corrected to be time phase data T2'.

$$T2'=\{T2-\Delta T(P2)-T(P1)\}\{T(P3)-T(P1)\}/\{T(P4)-T(P2)\}+T(P1) \quad (3)$$

When the above-mentioned interpolation processing of time phases is performed, the first time phase T(P1) at the first position P1 on the first blood vessel image data coincides with the second time phase T(P2) at the second position P2 on the second blood vessel image data while the third time phase T(P3) at the third position P3 on the first blood vessel image data coincides with the fourth time phase T(P4) at the fourth position P4 on the second blood vessel image data. Therefore, on the condition that a change in blood flow is due to a difference in position of a catheter and/or a velocity of the blood flow, the change in the blood flow is corrected by the correction processing of time phase data.

On the contrary, when a velocity of a blood flow has changed, before and after the treatment, due to removing a thrombus, the change in the blood flow is not corrected. As a result, as shown in (E) of FIG. 11, a large difference appears between the fifth time phase T(P5) at the fifth position P5 on the first blood vessel image data and a time phase T'(P6) after the correction of the sixth time phase T(P6) at the sixth position P6 on the second blood vessel image data, as an effect of improving the blood flow.

Note that, displayed colors can also be corrected similarly by correcting time phase in a portion, having a continuous color phase change, of a color scale as shown in FIG. 9. In that case, time phase in the portion, having the continuous color phase change, of the color scale is visually translated in parallel and deformed by expansion and contraction, in the time phase direction.

Further, regions may also be designated instead of designating positions as described above. Furthermore, when each the first blood vessel image data and the second blood vessel image data are generated using a color scale having a periodic color phase change as shown in (C) of FIG. 3 or a monotonic color scale as shown in (B) of FIG. 3 and (B) of FIG. 5, synchronous processing of color scales and time phases as shown in FIG. 9 or FIG. 11 may be performed similarly.

The synchronous processing of color scales and time phases between the first blood vessel image data and the second blood vessel image data can also be performed by directly and manually designating time phase periods, during which the color scales and time phases should be synchronized, on the first blood vessel image data and the second blood vessel image data, respectively. Each of the time phase periods which should be synchronized can be designated as a starting time phase and an ending time phase of a continuous change in color phase.

Figure 12:
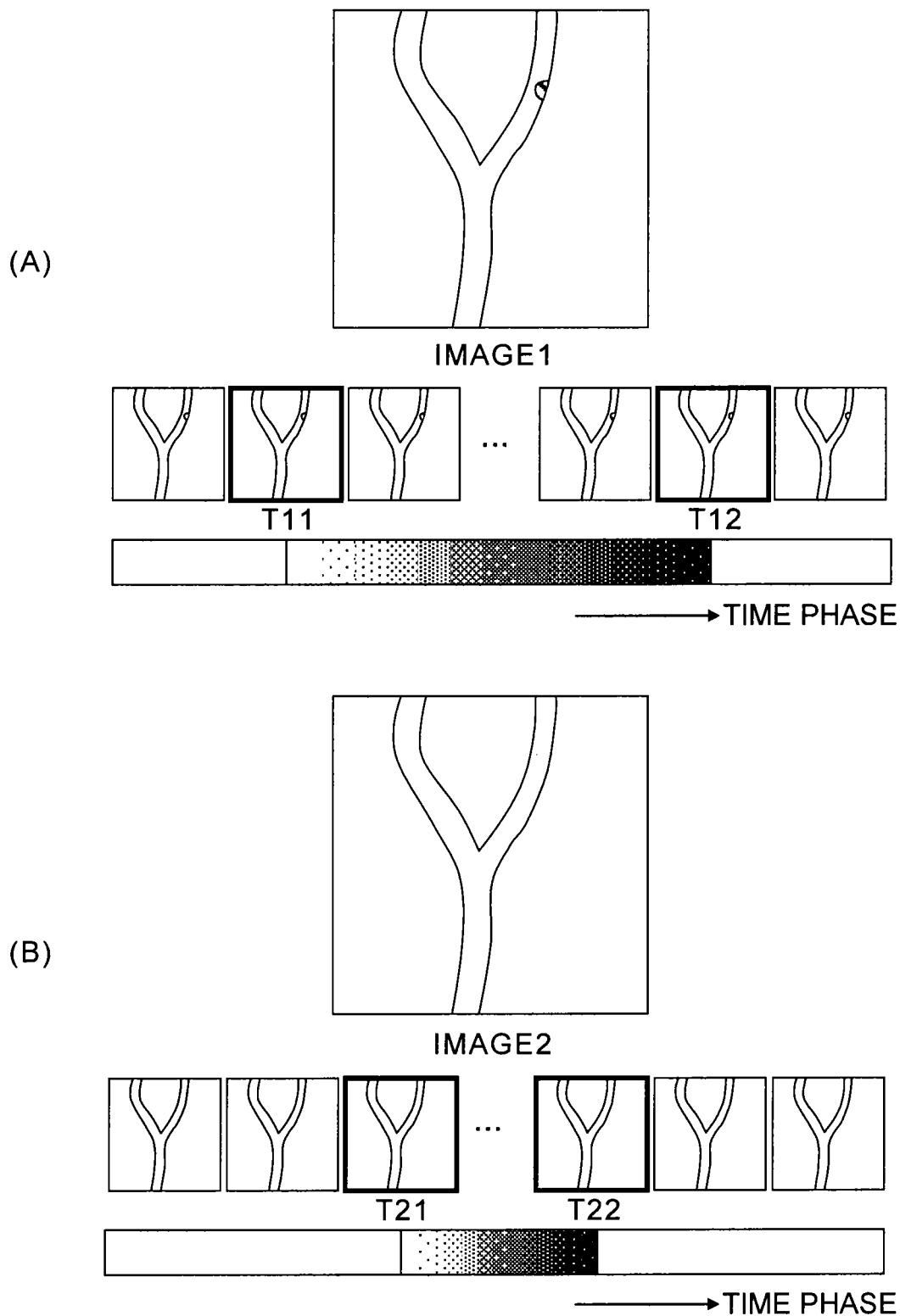
FIG. 12 shows an example of making colors in the time phase periods, which have been designated on the first blood vessel image data and the second blood vessel image data respectively, coincide between the first blood vessel image data and the second blood vessel image data.

FIG. 12 shows an example of making colors in the time phase periods, which have been designated on the first blood vessel image data and the second blood vessel image data respectively, coincide between the first blood vessel image data and the second blood vessel image data.

(A) of FIG. 12 shows an example of designating an initial time phase T11 and an ending time phase T12 of a continuous change in color phase of a color scale, as the first period, by selecting the time series first DSA image data or the time series first X-ray contrast image data. Meanwhile, (B) of FIG. 12 shows an example of designating an initial time phase T21 and an ending time phase T22 of a continuous change in color phase of a color scale, as the second period, by selecting the time series second DSA image data or the time series second X-ray contrast image data.

In this case, pixel values of at least one of the first blood vessel image data and the second blood vessel image data can be determined or corrected so that the first continuous change in pixel value assigned to the first period designated for generating the first blood vessel image data corresponds to the second continuous change in pixel value assigned to the second period designated for generating the second blood vessel image data. Specifically, the first change in pixel value can correspond to the second change in pixel value by making a pixel value at the initial time phase T11 of the first period coincide with a pixel value at the initial time phase T21 of the second period, and setting a period Tscale1 of the first change in pixel value to a different period from a period Tscale2 of the second change in pixel value. The period Tscale1 of the first change in pixel value and the period Tscale2 of the second change in pixel value are adjusted so that a pixel value at the end time phase T12 of the first period coincides with a pixel value at the end time phase T22 of the second period.

That is, a color scale for the first blood vessel image data and a color scale for the second blood vessel image data can be determined by manually designating time phases so that relationships between time phases and pixel values correspond to each other. Therefore, when the initial time phases T11 and T21 are set to inflow time phases of a contrast agent and the ending time phases T12 and T22 are set to the maximum values of concentrations or outflow time phases of the contrast agent, color coding processing can be performed selectively in time phase periods which are comparison targets. Furthermore, change rates of pixel values to the lengths of the time phase periods can coincide with each other. As a result, same parts which do not change between the first blood vessel image data and the second blood vessel image data can be displayed in same colors.

Note that, color synchronous processing can also be performed by another method by which only the initial time phases T11 and T21 of changes in pixel values can be designated to the first blood vessel image data and the second blood vessel image data respectively by selecting time series DSA image data or time series X-ray contrast image data, and subsequently the periods Tscale1 and Tscale2 of the changes in pixel values are made identical between the first blood vessel image data and the second blood vessel image data.

A variety of the synchronous processing of color display as described above can be switched by ON/OFF of synchronization switches disposed on the console 5 as electronic keys or hard keys. Furthermore, the synchronous processing of color display may be applied to not less than three frames of blood vessel image data. Specifically, when an instruction to switch a synchronization switch to the ON state has been input to the color synchronization display processing part 25 by operating the console 5, the color synchronization display processing part 25 can perform the synchronous processing of color display to frames of blood vessel image data by a designated processing method. Meanwhile, when an instruction to switch the synchronization switch to the OFF state has been input to the color synchronization display processing part 25 by operating the console 5, the color synchronization display processing part 25 can perform an independent color display for every blood vessel image data.

When a condition influencing the color coding has been changed while the synchronization switch is in the ON state, the color synchronization display processing part 25 can perform re-synchronous processing of color display, following the changed condition. For example, when the fourth position P4 shown in (A) of FIG. 11 or the ending time phase T12 shown in FIG. 12 has been changed, color coding processing for synchronization display can be performed again according to the changed fourth position P4 or the changed ending time phase T12. Then, the above-mentioned color synchronization display allows a user to compare frames of blood vessel image data acquired at different times and dates, and to visually observe changes in blood flows as changes in color.

The time phase difference image creation part 26 of the parametric image generation part 21 has a function to generate subtraction image data having pixel values corresponding to differences in time phases, at which concentrations of a contrast agent become a specific condition, between the first blood vessel image data and the second blood vessel image data, each generated as parametric image data. That is, the time phase difference image creation part 26 can obtain two dimensional time phase difference map data by subtraction processing between the first two dimensional time phase map for color coding of the first blood vessel image data and the second two dimensional time phase map for color coding of the second blood vessel image data. Then, time phase difference image data can be generated in color by color coding of the two dimensional time phase difference map data according to a desired color scale. That is, time phase difference image data can be generated as subtraction image data of two frames of parametric image data.

In the time phase difference image data, data are canceled at positions at which arrival time phases of a contrast agent did not change between the first blood vessel image data and the second blood vessel image data. Therefore, only portions which have changes in the arrival time phases of the contrast agent between the first blood vessel image data and the second blood vessel image data, that is, portions at which temporal changes have occurred are displayed in colors depending on degrees of the changes. Thereby, the first blood vessel image data can be quantitatively compared with the second blood vessel image data.

Note that, it is desirable to perform correction processing of time phases for making time phases of the first blood vessel image data correspond to time phases of the second blood vessel image data by the color synchronization display processing part 25, before the subtraction processing. Thereby, it becomes possible to meet differences in velocities of blood flows or the like. However, when an expansion and contraction correction of time phase period is unnecessary, such as a case where only positions of a catheter differ, time phase difference image data having pixel values depending on degrees of temporal changes can be generated even when the correction processing of the time phases are not performed as preprocessing of the subtraction processing.

Whether generation processing of time phase difference image data is necessary or not can also be directed with a comparison switch prepared similarly to the synchronization switch. In that case, when time phases have been corrected by changing a condition, time phase difference image data can be updated following the correction of the time phases.

In the X-ray diagnostic apparatus 1 and the medical image processing apparatus 12 having the functions and configurations as described above, the imaging system 2 and the control system 3 cooperating with each other function as an image acquisition system configured to acquire at least X-ray contrast image data from the object O. Furthermore, the time phase specifying part 22 and the color coding part 23, cooperating with each other, of the parametric image generation part 21 function as a blood vessel image generation part configured to obtain the first blood vessel image data and the second blood vessel image data by performing image generation processing multiple times based on X-ray contrast image data sets acquired at different times. The image generation processing obtains time phase changes in concentrations of a contrast agent based on at least X-ray contrast image data, and generates time phase image data, having pixel values corresponding to time phases at which the concentrations of the contrast agent become a specific condition, according to a gray scale or a color scale. The first blood vessel image data can be obtained based on X-ray contrast image data acquired before a treatment of the object O, for example. Meanwhile, the second blood vessel image data can be obtained based on X-ray contrast image data acquired after the treatment of the object O, for example.

Furthermore, the color coding part 23, the color scale adjustment part 24, and the color synchronization display processing part 25 cooperating with each other function as a pixel value determination part configured to determine or correct pixel values of at least one of the first blood vessel image data and the second blood vessel image data so that pixel values of time phases of the first blood vessel image data coincide with pixel values of corresponding time phases of the second blood vessel image data.

Note that, time phases (time) of blood vessel image data may be determined or corrected in the pixel value determination part, instead of pixel values of the blood vessel image data. Furthermore, both pixel values and time phases (time) of blood vessel image data may also be determined or corrected in the pixel value determination part. That is, at least one of pixel values and time phases (time) of blood vessel image data can be determined or corrected in the pixel value determination part.

On the other hand, the time phase difference image creation part 26 functions as a subtraction image generation part configured to generate subtraction image data having pixel values corresponding to differences in time phases, at which concentrations of a contrast agent become a specific condition, between the first blood vessel image data and the second blood vessel image data.

In addition, the color scale adjustment part 24 of the parametric image generation part 21 functions as a pixel value scale generation part configured to generate a color scale by assigning a continuous change in pixel value to a period, designated from a period from the initial time to the ending time of the time changes in the concentrations of the contrast agent, or the like.

Note that, the X-ray diagnostic apparatus 1 and the medical image processing apparatus 12 may be configured by other elements so long as similar functions as the image acquisition system, the blood vessel image generation part, the pixel value determination part, and the pixel value scale generation part are provided in the X-ray diagnostic apparatus 1 and the medical image processing apparatus 12. For example, the medical image processing apparatus 12 may be configured by installing a medical image processing program, which makes a computer function as the blood vessel image generation part, the pixel value determination part, and the pixel value scale generation part, to the computer. In that case, the medical image processing program can be recorded in an information recording medium to be distributed as a program product so that a general purpose computer can be used as the medical image processing apparatus 12.

Next, an operation and an action of the X-ray diagnostic apparatus 1 and the medical image processing apparatus 12 will be described. An example case where the second blood vessel image data are acquired after acquiring the first blood vessel image data, and subsequently, color synchronization display and generation of time phase difference image data are performed will be described here.

Figure 13:
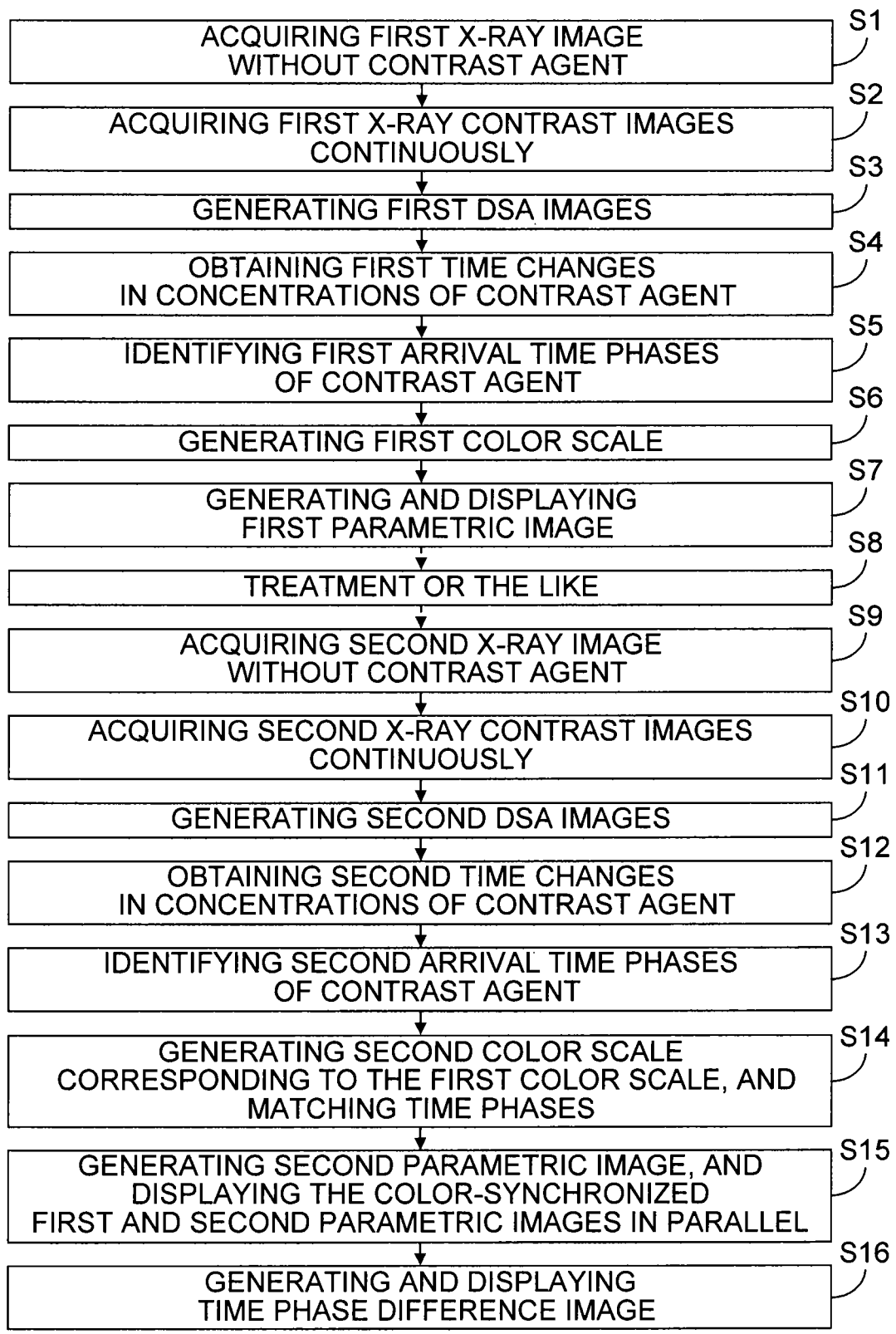
FIG. 13 is a flow chart which shows an operation of the X-ray diagnostic apparatus shown in FIG. 1 and processing in the medical image processing apparatus shown in FIG. 1.

FIG. 13 is a flow chart which shows an operation of the X-ray diagnostic apparatus 1 shown in FIG. 1 and processing in the medical image processing apparatus 12 shown in FIG. 1.

First, in step S1, the first X-ray image data are acquired without a contrast agent. Specifically, the imaging system 2 moves to a predetermined position and an X-ray is exposed from the X-ray tube 6 towards an object O set on the bed 10, under control by the control system 3. Then, the X-ray which has transmitted the object O is acquired as X-ray projection data by the X-ray detector 7. The X-ray projection data acquired by the X-ray detector 7 are output as the first X-ray image data to the medical image processing apparatus 12 through the A/D converter 11.

The first X-ray image data may be acquired for one frame or multiple frames. When multiple frames of the first X-ray image data are acquired and the average of the multiple frames of the first X-ray image data is calculated in the filtering part 18, one frame of non-contrast X-ray image data whose noises have been dramatically suppressed can be generated. Subsequently, the first non-contrast X-ray image data acquired as mentioned above are stored in the image memory 16.

Next, in step S2, the first X-ray contrast image data are acquired continuously. For that purpose, the contrast agent injector 15 operates under a control by the control system 3, and a contrast agent is injected into the object O. Subsequently, after a preset time has passed from the start time of the contrast agent injection, the acquisition of the first X-ray contrast image data starts. Then, the acquisition of the first X-ray contrast image data is performed continuously in a predetermined period. Thereby, the time series first X-ray contrast image data are stored sequentially in the image memory 16. The flow of acquiring the first X-ray contrast image data is similar to the flow of acquiring the first non-contrast X-ray image data.

Next, in step S3, the first DSA image data are generated by the subtraction part 17. More specifically, the time series first DSA image data are generated sequentially by subtraction processing of the time series first X-ray contrast image data using the first non-contrast X-ray image data as mask image data. The generated time series first DSA image data are stored sequentially in the image memory 16.

The time series first X-ray contrast images or the time series first DSA images can be displayed as live images in real time on the display 14. Furthermore, the time series first X-ray contrast images or the time series first DSA images can be also displayed on the display 14 after the X-ray imaging. When the first DSA images are displayed afterward, the first DSA image data can be generated by performing subtraction processing for only a time phase period designated by an operation of the console 5.

Next, in step S4, the first time changes in concentrations of the contrast agent are acquired by the time phase specifying part 22. Specifically, the time series first X-ray contrast image data or the time series first DSA image data in a time phase period designated by operations of the console 5 are taken into the time phase specifying part 22. Then, a concentration profile showing the first time change in concentration of the contrast agent as shown in (A) of FIG. 3 or (A) of FIG. 5 is generated for every pixel position in the time phase specifying part 22.

Note that, the filtering part 18 can perform one or both of low-pass filtering processing and running average processing in one or both of spatial directions and the time direction, as preprocessing or postprocessing of the generation of the concentration profiles of the contrast agent. Thereby, smooth concentration profiles, of the contrast agent, having reduced noises can be generated. In addition, concentration profiles of the contrast agent whose data intervals are shorter than sampling intervals can also be generated by interpolation processing, gravity center calculation, or curve fitting in the time phase specifying part 22.

Next, in step S5, the first arrival time phases of the contrast agent at the respective pixel positions are identified, by the time phase specifying part 22, based on the concentration profiles of the contrast agent. Specifically, the first arrival time phase of the contrast agent can be identified for every pixel position by data processing, such as peak detection processing or threshold value processing, of the concentration profiles of the contrast agent.

Note that, after the time phases have been specified by the data processing such as peak detection processing or threshold value processing, continuous concentration profiles only in periods close to the specified time phases may be generated by interpolation processing, gravity center calculation, or curve fitting. In that case, the true arrival time phases of the contrast agent are determined by data processing, such as peak detection processing or threshold value processing, of the generated continuous concentration profiles, for the second time.

Next, in step S6, the color scale adjustment part 24 generates the first color scale for color coding of a two dimensional map of the first arrival time phases of the contrast agent acquired by the time phase specifying part 22. The color scale adjustment part 24 can generate not only a general color scale whose color phase changes continuously from the initial time phase to the last time phase at a constant rate of change as shown in (B) of FIG. 3 or (B) of FIG. 5 but also a color scale as shown in (C) of FIG. 3 or (C) of FIG. 5 by increasing a change rate in color phase of a normal color scale.

In a case of generating a color scale whose color phase changes continuously and periodically as shown in (C) of FIG. 3, the color scale can be generated by specifying the period Tscale, in which the color phase changes, and changing the color phase in each period Tscale, by an operation of the console 5. Alternatively, these necessary conditions may be previously set as default values. A color phase at the starting time phase in each period Tscale can be designated arbitrarily. Furthermore, when a color phase at the initial time phase of concentration changes of a contrast agent is not set to a color phase at the starting time phase in each period Tscale, the color phase at the initial time phase needs to be designated.

Meanwhile, in a case of generating a color scale having a continuous color phase change, within a designated time phase period, different from that outside the designated time phase period, as shown in (C) of FIG. 5, the color scale can be generated by designating the starting time phase T1 and the ending time phase T2 of the time phase period, to which the continuous color phase change is assigned, by operation of the console 5. The starting time phase T1 and the ending time phase T2 can be designated by selecting an image from the time series X-ray contrast images or the time series DSA images displayed on the display 14 by operation of the console 5.

Next, in step S7, the color coding part 23 performs color coding, of the two dimensional map of the first arrival time phases of the contrast agent, based on the first color scale generated by the color scale adjustment part 24. Specifically, an R value, a G value, and a B value corresponding to the first arrival time phase of the contrast agent are assigned to each pixel, as pixel values, according to the color scale. Thereby, the first parametric image data are generated.

At this time, it is desirable to multiply each of the R value, the G value and the B value by a coefficient corresponding to a concentration of the contrast agent at the first arrival time phase of the contrast agent. Thereby, the first parametric image data can be generated so that a brightness value at a pixel, at which a concentration of the contrast agent at the first arrival time phase of the contrast agent is relatively high, is relatively high while a brightness value at a pixel, at which a concentration of the contrast agent at the arrival time phase of the contrast agent is relatively low, is relatively low.

Then, the first parametric image generated as described above can be displayed on the display 14. The first parametric image can also be displayed as a moving image by shifting, and/or expanding or contracting the first color scale in the time phase direction. Consequently, observing the first parametric image allows a user to recognize blood vessels into which a contrast agent flows. In particular, a color phase change in the first color scale has been assigned to a short time phase period, and therefore, blood vessels in which arrival time phases of a contrast agent are near to each other can be easily distinguished by a difference in color.

When the acquisition of the first parametric image ends, a treatment or the like can be performed in step S8. After that, acquisition of the second parametric image for a follow-up of the object O can be started at time and date different from the imaging time and date of the first parametric image.

In that case, in step S9 to step S13, the second non-contrast X-ray image data, the time series second X-ray contrast image data, the time series second DSA image data, the second time changes in concentrations of the contrast agent, and two dimensional map data of the second arrival time phases of the contrast agent are obtained in a flow similar to that for the acquisition of the first parametric image.

Then, in step S14, the second color scale corresponding to the first color scale is generated, and necessary time phase matching between the first parametric image and the second parametric image is performed by the color coding part 23, the color scale adjustment part 24, and the color synchronization display processing part 25. Specifically, one or both of the color scales and the time phases are adjusted in order to make pixel values of time phases of the first parametric image coincident with pixel values of corresponding time phases of the second parametric image, as exemplified in FIG. 8, FIG. 9, FIG. 11, or FIG. 12, according to a designated condition setting method. For that purpose, the second parametric image data may also be generated and displayed once according to a prepared color scale.

Next, in step S15, the two dimensional map data of the second arrival time phases of the contrast agent after the time phase adjustment are given to the color coding part 23. Then, the color coding part 23 performs color coding processing of the two dimensional map data of the second arrival time phases of the contrast agent after the time phase adjustment, according to the second color scale corresponding to the first color scale. Thereby, the second parametric image data are generated.

The generated second parametric image data are output to the display 14 together with the first parametric image data. Thereby, the first parametric image and the second parametric image are displayed in parallel on the display 14. At this time, the pixel values of the time phases of the first parametric image have coincided with the pixel values of the corresponding time phases of the second parametric image. Therefore, blood vessels which do not have change between the first parametric image and the second parametric image are displayed in the same colors while a blood vessel which has a change is displayed in different colors. Thereby, the user can observe a temporal change by a difference in color.

Next, in step S16, subtraction processing of the two dimensional map data of the first arrival time phases of the contrast agent after the time phase correction and the two dimensional map data of the second arrival time phases of the contrast agent after the time phase correction is performed by the time phase difference image creation part 26. As a result, two dimensional time phase difference map data are obtained. In the two dimensional time phase difference map data, data exist only at portions where substantial changes in the arrival time phases of the contrast agent have occurred. Then, the two dimensional time phase difference map data are color-coded according to a desired color scale in the color coding part 23. Thereby, color time phase difference image data are generated. The generated time phase difference image data are displayed on the display 14. Therefore, the user can visually perform a quantitative evaluation of a temporal change by colors of the time phase difference image data.

That is, the X-ray diagnostic apparatus 1 and the medical image processing apparatus 12 as described above are configured to generate blood flow image data in color by color coding of specific time phases, such as arrival time phases, of a contrast agent, with a color scale according to time phases and adjust time phases and color scales so that blood flow image data sets acquired at different times and dates can be compared with each other. In addition, the X-ray diagnostic apparatus 1 and the medical image processing apparatus 12 are configured to contract a continuous color phase change of the color scale in the time phase direction in order to improve time phase identification ability by color.

Therefore, the X-ray diagnostic apparatus 1 and the medical image processing apparatus 12 allow displaying a part, without a temporal change due to a treatment or the like, in a same color on parametric images acquired at different times and dates even when conditions, such as imaging timing, a position of a catheter for injecting a contrast agent, and a velocity of a blood flow, differ between the parametric images. That is, parametric images, on which a same color effectively shows a same time phase, can be displayed in parallel. Thereby, a user can compare parametric images, acquired at different times and dates, with each other. Furthermore, a user can also perform a quantitative evaluation of a temporal change caused by a treatment or the like, by a color display of time phase difference image data.

In addition, according to the X-ray diagnostic apparatus 1 and the medical image processing apparatus 12, adjacent blood vessels can be easily distinguished as a difference in color phase even when a difference in inflow time phase, arrival time phase or outflow time phase of a contrast agent is small among the blood vessels.

In particular, it is important to observe a blood flow into a diseased part between arteries and veins, in a diagnosis of a cerebral arteriovenous malformation or a dural arteriovenous fistula. Therefore, it is necessary to distinguish blood vessels into which a contrast agent flows. However, DSA images are displayed with a gray scale, and therefore, distinguishing contrast-enhanced blood vessels is difficult.

In contrast, the X-ray diagnostic apparatus 1 and the medical image processing apparatus 12 are configured to be able to set a period of a color phase change in a color scale to be short, according to a time phase difference which should be identified. Accordingly, colors change for every blood vessel even when a contrast agent flows into focused blood vessels almost simultaneously. Therefore, the blood vessels can be easily distinguished.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, an example case of generating blood vessel image data as color parametric image data, using a color scale, has been described in the embodiment described above. Alternatively, blood vessel image data may also be generated using a gray scale. Specifically, time phase image data and time phase difference image data each having pixel values corresponding to times when concentrations of a contrast agent become a specific condition can be generated according to a gray scale or a color scale. Furthermore, a gray scale or a color scale can be generated by assigning a change in pixel value to a period shorter than the period from the initial time to the ending time of time changes in concentrations of a contrast agent.

When time phase image data or time phase difference image data are generated using a gray scale, a continuous change in brightness value instead of a color phase change is to be assigned, as a change in pixel value, to a period shorter than the period from the initial time to the ending time of time changes in concentrations of a contrast agent. In that case, each brightness value can also be set to a value according to a concentration of the contrast agent by multiplying the brightness value by a coefficient k according to the concentration of the contrast agent.

Similarly, when time phase image data or time phase difference image data are generated using a color scale, not only a continuous color phase change but a continuous change in brightness value can also be assigned as a change in pixel value as described above. In that case, each brightness value can also be set to a value according to a concentration of a contrast agent by multiplying the brightness value by a coefficient k according to the concentration of the contrast agent.

As described above, a change in pixel value assigned to a period shorter than the period from the initial time to the ending time of time changes in concentrations of a contrast agent may be a continuous color phase change, a continuous change in color brightness value, or a continuous change in gray brightness value.

In addition, the X-ray diagnostic apparatus 1 of which the X-ray tube 6 and the X-ray detector 7 have been fixed to the both ends of the C-shaped arm 8 has been exemplified in the embodiment described above. Similarly, an X-ray diagnostic apparatus having another structure can also generate parametric image data. Examples of an X-ray diagnostic apparatus having another structure include an X-ray diagnostic apparatus of which each of the X-ray tube 6 and the X-ray detector 7 is fixed to an independent arm, besides an X-ray diagnostic apparatus having multiple arms or an X-ray diagnostic apparatus including movement structures for moving arbitrary arms along axes in arbitrary directions, such as an arc axis or a straight axis. When each of the X-ray tube 6 and the X-ray detector 7 is fixed to an independent arm, it is practical to install driving structures, such as an expansion and contraction structure, a rotating structure, a joint structure and a link mechanism, on each of the first arm holding the X-ray tube 6 and the second arm holding the X-ray detector 7.

What is claimed is:

1. A medical image processing apparatus comprising:
processing circuitry configured to
obtain first blood vessel image data and second blood vessel image data by image generation processing which obtains time phase changes in concentrations of a contrast agent based on at least X-ray contrast image data and generates time phase image data according to a gray scale or a color scale, the time phase image data having pixel values corresponding to time phases at which the concentrations of the contrast agent become a specific condition, the image generation processing being performed multiple times, the first blood vessel image data being first time phase image data generated by the image generation processing based on at least first X-ray contrast image data set acquired with a first injection of a first contrast agent at a first time, and the second blood vessel image data being second time phase image data generated by the image generation processing based on at least second X-ray contrast image data set acquired with a second injection of a second contrast agent at a second time;
determine or correct pixel values or time phases of at least one of the first blood vessel image data and the second blood vessel image data, in order to make a pixel value of a time phase of the first blood vessel image data coincident with a pixel value of a corresponding time phase of the second blood vessel image data; and
display at least one of the first blood vessel image data and the second blood vessel image data to evaluate a blood vessel, wherein
the processing circuitry is configured to correct the pixel values or the time phases of the at least one of the first blood vessel image data and the second blood vessel image data, in order to make a pixel value of a first time phase in a first region or at a first position designated by a user on the first blood vessel image data coincident with a pixel value of a second time phase in a second region or at a second position on the second blood vessel image data, the second region or the second position corresponding to the first region or the first position respectively.

2. The medical image processing apparatus of claim 1, wherein the processing circuitry is configured to
obtain the first blood vessel image data based on X-ray contrast image data acquired before a treatment of an object; and
obtain the second blood vessel image data based on X-ray contrast image data acquired after the treatment of the object.

3. The medical image processing apparatus of claim 1, wherein the processing circuitry is configured to
obtain information for specifying a gray scale or a color scale used for generating the first blood vessel image data; and
determine or correct pixel values of the second blood vessel image data, according to a same gray scale or a same color scale as the gray scale or the color scale used for generating the first blood vessel image data, based on the obtained information.

4. The medical image processing apparatus of claim 1, wherein the processing circuitry is configured to correct the pixel values or the time phases of the at least one of the first blood vessel image data and the second blood vessel image data with interpolation processing, in order to make a pixel value of a third time phase in a third region or at a third position further designated on the first blood vessel image data coincident with a pixel value of a fourth time phase in a fourth region or at a fourth position on the second blood vessel image data, the fourth region or the fourth position corresponding to the third region or the third position respectively, the interpolation processing making time phases, between the first region and the third region or between the first position and the third position, correspond to time phases, between the second region and the fourth region or between the second position and the fourth position.

5. The medical image processing apparatus of claim 1, wherein the processing circuitry is configured to
generate the gray scale or the color scale by assigning a continuous change in pixel value to a period designated from a period from an initial time phase to an ending time phase of the time phase changes in the concentrations of the contrast agent; and
correct the pixel values or the time phases of the at least one of the first blood vessel image data and the second blood vessel image data, in order to make a first continuous change in pixel value assigned to a first period designated for generating the first blood vessel image data correspond to a second continuous change in pixel value assigned to a second period designated for generating the second blood vessel image data.

6. The medical image processing apparatus of claim 5, wherein the processing circuitry is configured to make the first continuous change in the pixel value correspond to the second continuous change in the pixel value, by making a pixel value at an initial time phase in the first period coincident with a pixel value at an initial time phase in the second period and making a period of the first continuous change in the pixel value different from a period of the second continuous change in the pixel value.

7. The medical image processing apparatus of claim 5, wherein the processing circuitry is configured to generate the gray scale or the color scale by assigning a continuous change in color phase, a continuous change in at least one color brightness value or a continuous change in gray brightness value, as the continuous change in the pixel value.

8. The medical image processing apparatus of claim 1, wherein the processing circuitry is configured to generate subtraction image data having pixel values corresponding to differences in the time phases, at which the concentrations of the contrast agent become the specific condition, between the first blood vessel image data and the second blood vessel image data.

9. The medical image processing apparatus of claim 1, wherein the processing circuitry is configured to generate time phase image data having brightness values according to concentrations of the contrast agent at the specific condition.

10. The medical image processing apparatus of claim 1, wherein the specific condition is maximum values, a predetermined ratio of the maximum values, or a threshold value.

11. The medical image processing apparatus of claim 1, wherein the processing circuitry is configured to generate the time phase image data based on time phase changes, in the concentrations of the contrast agent, having a data interval shorter than a sampling interval of the concentrations of the contrast agent.

12. A medical image processing apparatus comprising:
processing circuitry configured to
obtain first blood vessel image data and second blood vessel image data by image generation processing which obtains time phase changes in concentrations of a contrast agent based on at least X-ray contrast image data and generates time phase image data according to a gray scale or a color scale, the time phase image data having pixel values corresponding to time phases at which the concentrations of the contrast agent become a specific condition, the image generation processing being performed multiple times, the first blood vessel image data being first time phase image data generated by the image generation processing based on at least first X-ray contrast image data set acquired with a first injection of a first contrast agent at a first time, and the second blood vessel image data being second time phase image data generated by the image generation processing based on at least second X-ray contrast image data set acquired with a second injection of a second contrast agent at a second time,
generate subtraction image data having pixel values corresponding to differences in the time phases, at which the concentrations of the contrast agent become the specific condition, between the first blood vessel image data and the second blood vessel image data, and
display the subtraction image to evaluate a blood vessel.

13. An X-ray diagnostic apparatus comprising:
an X-ray tube and an X-ray detector for acquiring at least X-ray contrast image data from an object; and
processing circuitry configured to
obtain first blood vessel image data and second blood vessel image data by image generation processing which obtains time phase changes in concentrations of a contrast agent based on the at least X-ray contrast image data and generates time phase image data according to a gray scale or a color scale, the time phase image data having pixel values corresponding to time phases at which the concentrations of the contrast agent become a specific condition, the image generation processing being performed multiple times, the first blood vessel image data being first time phase image data generated by the image generation processing based on at least first X-ray contrast image data set acquired with a first injection of a first contrast agent at a first time, and the second blood vessel image data being second time phase image data generated by the image generation processing based on at least second X-ray contrast image data set acquired with a second injection of a second contrast agent at a second time,
determine or correct pixel values or time phases of at least one of the first blood vessel image data and the second blood vessel image data, in order to make a pixel value of a time phase of the first blood vessel image data coincident with a pixel value of a corresponding time phase of the second blood vessel image data, and
display at least one of the first blood vessel image data and the second blood vessel image data to evaluate a blood vessel, wherein
the processing circuitry is configured to correct the pixel values or the time phases of the at least one of the first blood vessel image data and the second blood vessel image data, in order to make a pixel value of a first time phase in a first region or at a first position designated by a user on the first blood vessel image data coincident with a pixel value of a second time phase in a second region or at a second position on the second blood vessel image data, the second region or the second position corresponding to the first region or the first position respectively.

14. A medical image processing method comprising:
obtaining first blood vessel image data and second blood vessel image data by image generation processing which obtains time phase changes in concentrations of a contrast agent based on at least X-ray contrast image data and generates time phase image data according to a gray scale or a color scale, the time phase image data having pixel values corresponding to time phases at which the concentrations of the contrast agent become a specific condition, the image generation processing being performed multiple times, the first blood vessel image data being first time phase image data generated by the image generation processing based on at least first X-ray contrast image data set acquired with a first injection of a first contrast agent at a first time, the second blood vessel image data being second time phase image data generated by the image generation processing based on at least second X-ray contrast image data set acquired with a second injection of a second contrast agent at a second time;
determining or correcting pixel values or time phases of at least one of the first blood vessel image data and the second blood vessel image data, in order to make a pixel value of a time phase of the first blood vessel image data coincident with a pixel value of a corresponding time phase of the second blood vessel image data; and
displaying at least one of the first blood vessel image data and the second blood vessel image data to evaluate a blood vessel, wherein
the determining or correcting corrects the pixel values or the time phases of the at least one of the first blood vessel image data and the second blood vessel image data, in order to make a pixel value of a first time phase in a first region or at a first position designated by a user on the first blood vessel image data coincident with a pixel value of a second time phase in a second region or at a second position on the second blood vessel image data, the second region or the second position corresponding to the first region or the first position respectively.

15. An X-ray diagnostic method comprising:
acquiring at least X-ray contrast image data from an object;
obtaining first blood vessel image data and second blood vessel image data by image generation processing which obtains time phase changes in concentrations of a contrast agent based on the at least X-ray contrast image data and generates time phase image data according to a gray scale or a color scale, the time phase image data having pixel values corresponding to time phases at which the concentrations of the contrast agent become a specific condition, the image generation processing being performed multiple times, the first blood vessel image data being first time phase image data generated by the image generation processing based on at least first X-ray contrast image data set acquired with a first injection of a first contrast agent at a first time, the second blood vessel image data being second time phase image data generated by the image generation processing based on at least second X-ray contrast image data set acquired with a second injection of a second contrast agent at a second time;
determining or correcting pixel values or time phases of at least one of the first blood vessel image data and the second blood vessel image data, in order to make a pixel value of a time phase of the first blood vessel image data coincident with a pixel value of a corresponding time phase of the second blood vessel image data; and
displaying at least one of the first blood vessel image data and the second blood vessel image data to evaluate a blood vessel, wherein
the determining or correcting corrects the pixel values or the time phases of the at least one of the first blood vessel image data and the second blood vessel image data, in order to make a pixel value of a first time phase in a first region or at a first position designated by a user on the first blood vessel image data coincident with a pixel value of a second time phase in a second region or at a second position on the second blood vessel image data, the second region or the second position corresponding to the first region or the first position respectively.

* * * * *

UNITED STATES PATENT AND TRADEMARK OFFICE
CERTIFICATE OF CORRECTION

PATENT NO. : 10,702,231 B2
APPLICATION NO. : 14/878662
DATED : July 7, 2020
INVENTOR(S) : Satoru Ohishi It is certified that error appears in the above-identified patent and that said Letters Patent is hereby corrected as shown below:

On the Title Page

Item (73), the Assignee's information is incorrect. Item (73) should read:
--(73) Assignee: Canon Medical Systems Corporation, Otawara-shi (JP)--

Signed and Sealed this
Eighteenth Day of August, 2020

Andrei Iancu
*Director of the United States Patent and Trademark Office*